US009119805B2

(12) United States Patent
McGregor et al.

(10) Patent No.: US 9,119,805 B2
(45) Date of Patent: Sep. 1, 2015

(54) THERAPY AND PREVENTION OF PROBLEM DRINKING

(75) Inventors: Iain Stewart McGregor, Sydney (AU);
Dean Samuel Carson, Sydney (AU);
Adam John Guastella, Sydney (AU);
Michael Thomas Bowen, Sydney (AU)

(73) Assignee: THE UNIVERSITY OF SYDNEY, Sydney (AU)

( * ) Notice: Subject to any disclaimer, the term of this patent is extended or adjusted under 35 U.S.C. 154(b) by 0 days.

(21) Appl. No.: 13/499,654

(22) PCT Filed: Sep. 29, 2010

(86) PCT No.: PCT/AU2010/001275
§ 371 (c)(1),
(2), (4) Date: Jun. 21, 2012

(87) PCT Pub. No.: WO2011/038451
PCT Pub. Date: Apr. 7, 2011

(65) Prior Publication Data
US 2012/0270785 A1    Oct. 25, 2012

(30) Foreign Application Priority Data
Oct. 1, 2009    (AU) .............................. 2009904810

(51) Int. Cl.
*A61K 38/11*    (2006.01)

(52) U.S. Cl.
CPC ...................................... *A61K 38/11* (2013.01)

(58) Field of Classification Search
None
See application file for complete search history.

(56) References Cited

U.S. PATENT DOCUMENTS

2006/0252685 A1*    11/2006    Gould .............................. 514/12

OTHER PUBLICATIONS

Kovacs et al., Oxytocin and Addiction: A Review, Psychoneuroendocrinology, 1998, vol. 23, No. 8, pp. 945-962.*
Szabo et al., D-pipecolyl-leucyl-glycinamide, I substituted tripeptide analogue of the c-terminal part of oxytocin, influences tolerance to and dependence on ethanol in mice, Alcohol and Drug Research, vol. 7,, pp. 99-105, 1986.*
McGregor et al., From ultrasocial to antisocial: a role for oxytocin in the acute reinforcing effects and long-term adverse consequences of drug use?, Br. Jl. of Pharm., 154/2, pp. 358-368, May 2008 issue.*
Ansseau et al., Intranasal oxytocin in obsessive-compulsive disorder, Psychoneuroendocrinology, 1987;12(3):231-6, Abstract text.*
Szabo, G. et al., "D-Pipecolyl-Leucyl-Glycinamide, A Substituted Tripeptide Analogue of the C-Terminal Part of Oxytocin, Influences Tolerace to an Dependence on Ethaol in Mice", Alcohol and Drug Research, 1987, 7(2): 99-105.

Szabo, G. et al., "Effects of Neurohypophyseal Peptide Hormones on Alcohol Dependence and Withdrawal", Alcohol and Alcoholism, 1987, 22(1): 71-74.
Kovacs, G. et al., "Oxytocin and Addiction: A Review", Psychoneuroendocrinology, 1998, 23(8): 945-962.
Benelli, A. et al., "Oxytocin-Induced Inhibtition of Feeding and Drinking: No Sexual Dimorphism in Rats", Neuropeptides, 1991, 20:57-62.
McGregor, I., "From ultrasocial to antisocial: a role for oxytocin in the acute reinforcing effects and long-term adverse consequences of drug use?", British Jounral of Pharmacology, 2008, 154: 358-368.
File History of European Patent Application No. 10819736.9, EP Patent No. 2482835, downloaded Sep. 29, 2014.
Keane and Leonard (1989) "Rodent models of alcoholism: a review" Alcohol and Alcoholism, 24:299-309.
Spanagel (2000) "Recent Animal Models of alcoholism" Alcohol Research and Health, 24(2):124-131.
Bowen et al. (2011) "Adolescent oxytocin exposure causes persistent reduction in anxiety and alcohol consumption and enhances sociability in mice", Plos ONE, 6(11):1-11.
Pederson et al. (2013) "Intranasal oxytocin blocks alcohol withdrawal in Human subjects", Alcohol Clinc Exp Res, 37(3):484-489.
Carey, Robert, et al., "A Decrease in Ethanol Preference in Rats Resulting from Forced Ethanol Drinking Under Fluid Deprivation", Physiology and Behavior, 1972, 8:373-375.
Slawecki and Betancourt, et al., "Effects of adolescent ethanol exposure on ethanol consumption in adult rats" Alcohol, 2002, 26:23-30.
Spanagel, Ranier, et al. "Alchol addiction research: from animal models to clinics" Best Practice & Research Clinical Gastroenterology, 2003, 17(4):507-518.
Alcohol and Your Health, 2001, Australian Alcohol Guidelines (at https://www.nhmrc.gov.au/your-health/alcohol-guidlines) 10 pages.
Makkai, Toni and McAllister, Ian, 1998, "Patterns of Drug Use in Australia, 1985-95", Canberra: Department of Health and Family Services, 94 pages.
Alcohol consumption factsheet, 2014, Institute of Alcohol Studies, UK, (www.ias.org.uk), 17 pages.
"Low Risk alcohol drinking advice" from New Zealand, 2014, which is found at http://www.alcohol.org.nz/alcohol-you/your-drinking-okay/low-risk-alcohol-drinking-advice, 2 pages. Adams, Sam, 2014, "Don't drink alcohol two days in a row Government health quango warns" found at http://www.mirror.co.uk/news/uk-news/dont-drink-alcohol-two-days-4027125#ixzz3FyvftCp9, News article from UK (Mirror journal), 3 pages.
"RUPissed? The Online Breathalyser & BAC Calculator", 2014, http://www.rupissed.com/standarddrinks.html, 2 pages.
Alcohol Units per Week—Facts About Alcohol, 2014, "Recommended Safe Limits of Alcohol", Patient.co.uk, http://www.patient.co.uk/health/Recommended-Safe-Limits-of-Alcohol.htm, 3 pages.
Boismare, F., et al., (1984), "A homotaurine derivative reduces the voluntary intake of ethanol by rats: are cerebral GABA receptors involved", *Pharmacology Biochemistry and Behavior*, 21(5):787-789.
Carmen, B., et al., (2004), "Efficacy and safety of naltrexone and acamprosate in the treatment of alcohol dependence: a systematic review", *Addiction*, 99(7):811-828.

(Continued)

*Primary Examiner* — Karlheinz R Skowronek
*Assistant Examiner* — Joseph Fischer
(74) *Attorney, Agent, or Firm* — Carol L. Francis; Bozicevic, Field & Francis LLP

(57) ABSTRACT

The present invention provides methods for the therapy and prevention of problem drinking in alcohol-dependent and non-dependent subjects and those at risk of developing problem drinking behavior, and compositions of matter comprising oxytocin or an analog or derivative thereof or an agonist or partial agonist of an oxytocin receptor that are useful in preventing or treating problem drinking.

16 Claims, 8 Drawing Sheets

(56) References Cited

OTHER PUBLICATIONS

Chau, P., et al., (2010), "Glycine Receptors in the Nucleus Accumbens Involved in the Ethanol Intake-Reducing Effect of Acamprosate", *Alcoholism: Clinical and Experimental Research*, 34(1):39-45.

Cowen, M., et al., (2005), "The acute anti-craving effect of acamprosate in alcohol-preferring rats is associated with modulation of the mesolimbic dopamine system", *Addiction Biology*, 10(3):233-242.

Froehlich, J. C., et al., (2013), "Combining Naltrexone and Prazosin in a Single Oral Medication Decreases Alcohol Drinking More Effectively Than Does Either Drug Alone", *Alcoholism: Clinical and Experimental Research*, 37(10):1763-1770.

Gilpin, N. W., et al., (2008), "Effects of CRF1-Receptor and Opioid-Receptor Antagonists on Dependence-Induced Increases in Alcohol Drinking by Alcohol-Preferring (P) Rats", *Alcoholism: Clinical and Experimental Research*, 32(9):1535-1542.

Hargreaves, G. A., & McGregor, I. S., (2007), "Topiramate Moderately Reduces the Motivation to Consume Alcohol and Has a Marked Antidepressant Effect in Rats" *Alcoholism: Clinical and Experimental Research*, 31(11):1900-1907.

Henderson-Redmond, A., & Czachowski, C., (2014), "Effects of systemic opioid receptor ligands on ethanol- and sucrose seeking and drinking in alcohol-preferring (P) and Long Evans rats", Psychopharmacology, 231(22):4309-4321.

Hölter, S. M., et al., (1997), "Time Course of Acamprosate Action on Operant Ethanol Self-Administration after Ethanol Deprivation", *Alcoholism: Clinical and Experimental Research*, 21(5):862-868.

Johnson, B. A., et al, (2003), "Oral topiramate for treatment of alcohol dependence: a randomised controlled trial", *The Lancet*, 361(9370):1677-1685.

Lhuintre, J.-P., et al., (1985), "Ability of calcium bis acetyl homotaurine, a GABA agonist, to prevent relapse in weaned alcoholics", *The Lancet*, 325(8436):1014-1016.

MacDonald, Elayne, et al, (2011), "A review of safety, side-effects and subjective reactions to intranasal oxytocin in human research", *Psychoneuroendocrinology 36*: 1114-1126.

O'Malley, S. S., et al., (1996), "Six-month follow-up of naltrexone and psychotherapy for alcohol dependence", *Archives of General Psychiatry*, 53(3):217-224.

Volpicelli, J. R., et al, (1992), "NAltrexone in the treatment of alcohol dependence", *Archives of General Psychiatry*, 49(11):876-880.

Volpicelli, J. R., et al., (1986), "Naltrexone blocks the post-shock increase of ethanol consumption", *Life Sciences*, 38(9):841-847.

Whitworth, A., et al., (1996), "Comparison of acamprosate and placebo in long-term treatment of alcohol dependence", *The Lancet*, 347(9013):1438-1442.

Zalewska-Kaszubska, J., et al., (2013), "Effect of repeated treatment with topiramate on voluntary alcohol intake and beta-endorphin plasma level in Warsaw alcohol high-preferring rats", *Psychopharmacology*, 225(2):275-281.

Zalewska-Kaszubska, J., et al., (2008), "Effect of chronic acamprosate treatment on voluntary alcohol intake and β-endorphin plasma levels in rats selectively bred for high alcohol preference", *Neuroscience Letters*, 431(3):221-225.

\* cited by examiner

SEQUENCE LISTING

<160> NUMBER OF SEQ ID NOS: 11

<210> SEQ ID NO 1
<211> LENGTH: 9
<212> TYPE: PRT
<213> ORGANISM: homo sapiens

<400> SEQUENCE: 1

Cys Tyr Ile Gln Asn Cys Pro Leu Gly
1               5

<210> SEQ ID NO 2
<211> LENGTH: 9
<212> TYPE: PRT
<213> ORGANISM: artificial sequence
<220> FEATURE:
<223> OTHER INFORMATION: 4-threonine-1-hydroxy-deaminooxytocin

<400> SEQUENCE: 2

Cys Tyr Ile Thr Asn Cys Pro Leu Gly
1               5

<210> SEQ ID NO 3
<211> LENGTH: 9
<212> TYPE: PRT
<213> ORGANISM: artificial sequence
<220> FEATURE:
<223> OTHER INFORMATION: 4-serine, 8-isoleucine-oxytocin

<400> SEQUENCE: 3

Cys Tyr Ile Ser Asn Cys Pro Ile Gly
1               5

<210> SEQ ID NO 4
<211> LENGTH: 9
<212> TYPE: PRT
<213> ORGANISM: artificial sequence
<220> FEATURE:
<223> OTHER INFORMATION: 9-deamidooxytocin

<400> SEQUENCE: 4

Cys Tyr Ile Gln Asn Cys Pro Leu Gly
1               5

<210> SEQ ID NO 5
<211> LENGTH: 9
<212> TYPE: PRT
<213> ORGANISM: artificial sequence
<220> FEATURE:
<223> OTHER INFORMATION: 7-D-proline-oxytocin

<400> SEQUENCE: 5

Cys Tyr Ile Gln Asn Cys Pro Leu Gly
1               5

<210> SEQ ID NO 6
<211> LENGTH: 9
<212> TYPE: PRT
<213> ORGANISM: artificial sequence
<220> FEATURE:
<223> OTHER INFORMATION: (2,4-diisoleucine)-oxytocin

<400> SEQUENCE: 6

Cys Ile Ile Ile Asn Cys Pro Leu Gly
1               5

```
<210> SEQ ID NO 7
<211> LENGTH: 9
<212> TYPE: PRT
<213> ORGANISM: artificial sequence
<220> FEATURE:
<223> OTHER INFORMATION: 4-threonine, 7-glycine-oxytocin (TG-OT)

<400> SEQUENCE: 7

Cys Tyr Ile Thr Asn Cys Gly Leu Gly
1               5

<210> SEQ ID NO 8
<211> LENGTH: 9
<212> TYPE: PRT
<213> ORGANISM: artificial sequence
<220> FEATURE:
<223> OTHER INFORMATION: 3-phenylalanine-oxytocin (oxypressin)

<400> SEQUENCE: 8

Cys Tyr Phe Gln Asn Cys Pro Leu Gly
1               5

<210> SEQ ID NO 9
<211> LENGTH: 8
<212> TYPE: PRT
<213> ORGANISM: artificial sequence
<220> FEATURE:
<223> OTHER INFORMATION: carbetocin

<400> SEQUENCE: 9

Tyr Ile Gln Asn Cys Pro Leu Gly
1               5

<210> SEQ ID NO 10
<211> LENGTH: 7
<212> TYPE: PRT
<213> ORGANISM: artificial sequence
<220> FEATURE:
<223> OTHER INFORMATION: deamino-6-carba-oxytoxin(dC60)

<400> SEQUENCE: 10

Tyr Ile Gln Asn Pro Leu Gly
1               5

<210> SEQ ID NO 11
<211> LENGTH: 7
<212> TYPE: PRT
<213> ORGANISM: artificial sequence
<220> FEATURE:
<223> OTHER INFORMATION: deamino-di-carba-oxytoxin

<400> SEQUENCE: 11

Tyr Ile Gln Asn Pro Leu Gly
1               5
```

THERAPY AND PREVENTION OF PROBLEM DRINKING

CROSS-REFERENCE TO RELATED APPLICATION

This application is a national phase application of international application no. PCT/AU2010/001275, filed Sep. 29, 2010, which application claims the benefit of priority from Australian Patent Application No. 2009904810 filed Oct. 1, 2009, the contents of which are hereby incorporated in their entirety by reference.

FIELD OF THE INVENTION

The present invention relates to the field of therapy and prophylaxis of problem drinking including hazardous drinking and/or harmful drinking and/or one or more alcohol use disorders and/or one or more alcohol-related diseases.

BACKGROUND OF THE INVENTION

1. Description of the Related Art

Problem Drinking

Consumption of alcohol is an accepted part of modern life in most societies, and for most individuals, self-moderation of alcohol intake ensures that alcohol consumption is non-problematic with respect to posing adverse health or social consequence(s). For some individuals, alcohol consumption does not remain with safe limits within single sessions or over longer time periods and, for those individuals, problem drinking may develop.

As used herein, the term "problem drinking" means an acute or chronic alcohol consumption associated with the development of one or more life problems or adverse health effects, including actual adverse consequence(s) and an elevated risk thereof. Commonly, problem drinking is harmful and/or hazardous to any person, and/or likely to lead to alcohol dependency or constitute alcohol dependency in the consumer. Alcohol misuse is similar to hazardous drinking in so far as it refers to any alcohol consumption that is associated with risk, ranging from hazardous drinking to alcohol dependence.

Problem drinking imposes a significant burden to the individual in terms of reduced physical and/or mental and/or social health and well-being, as well as possible adverse economic effects. For example, problem drinkers suffer from or have increased risk relative to moderate drinkers of contracting any one or more of a number of diseases or conditions indicative of poor health e.g., fatty liver disease; hypermegaly of the liver; alcoholic hepatitis; cirrhosis of the liver; renal hypermegaly, renal failure; cancer, such as oesophageal cancer, lip cancer, oral cancer, pharyngeal cancer, laryngeal cancer or breast cancer; cardiovascular disease; coronary heart disease; hyperglycemia; hypoglycemia e.g., in diabetic subjects; hypertensive disease; ischemic heart disease; ischemic stroke; hemorrhagic stroke; gout; arthritis; protein-energy malnutrition e.g., as determined by deficiency in one or more of protein, calcium, iron, vitamin A, vitamin C, thiamine, vitamin B6 and riboflavin, and/or impaired absorption of one or more of calcium, phosphorus, vitamin D and zinc; neuropathy; dementia; impaired balance; impaired memory; depression; anxiety; or insomnia. Risk factors for cardiovascular disease e.g., elevated blood pressure and/or elevated high density lipoprotein (HDL) content, are well-documented side-effects of problem drinking. Impaired neuropsychological functioning may also promote risk-taking behavior e.g., unprotected sex, aggression, other substance misuse, as well as contribute to short-term memory dysfunction and/or long-term memory dysfunction in the problem drinker.

In addition to adverse effects and disease implications for problem drinkers, problem drinking in pregnant females may produce adverse consequences for their unborn fetus leading to one or more neonatal and/or childhood problems e.g., reduced birth weight, reduced active sleep period, growth deficit, central nervous system (CNS) dysfunction including impaired brain function, learning difficulty, mental retardation, craniofacial abnormality, poor host defense, elevated incidence and severity of infection, or long-lasting deficiency in humoral and/or cell-mediated immunity including B cell deficiency. Fetal alcohol syndrome (FAS) may develop in offspring exposed in utero to alcohol.

Alternatively, or in addition, there are obvious adverse social effects of problem drinking e.g., third party personal injury arising from machine use by problem drinkers when intoxicated or suffering from other problems of alcohol abuse, injury to property by problem drinkers, and abusive behavior. Problem drinking also carries significant social costs resulting e.g., from premature mortality, reduced health and income. For example, acute and chronic problem drinking leads to increased health care costs associated with treatment of injured or unwell individuals, and education programs to increase awareness of the problem or prevent problem drinking, as well as increased social security costs in supplementing lost income. The costs of social, health and welfare programs vary between countries, however it is not unusual for approximately 1-2% of GDP to be spent on the prevention or treatment of problem drinking in the OECD countries. For example, AUD 3.83 billion was spent in Australia in 1992 on treatment and/or prevention of problem drinking, accounting for 1.0% of that country's GDP.

Problem drinking is characterized by high frequency of alcohol intake and/or high level of alcohol consumption. Problem drinking includes any pattern of high alcohol consumption e.g., in single weekly sessions or during multiple days in one or more weeks, or over an extended period of time e.g., one or more months or over several years.

For example, problem drinking may be any acute or chronic excessive alcohol consumption that is sufficient to reduce the health of the consumer. For example, harmful drinking is an acute or chronic excessive alcohol consumption that has caused damage to health e.g., physical damage such as liver damage from chronic drinking or mental damage such as episodic depression secondary to drinking. Chronic alcohol abusers or misusers who consume excessive amounts of alcohol on a regular basis e.g., harmful or hazardous drinkers, may not demonstrate marked impairment at high blood alcohol levels however are more likely to suffer from long-term health defects.

Alternatively, or in addition, problem drinking is a pattern and/or level of alcohol consumption that is sufficient to increase a risk of disease in a subject. For example, hazardous drinking is any acute or chronic excessive alcohol consumption carrying with it a risk of harmful consequences to the drinker e.g., damage to physical or mental health, or social consequence to the drinker or others. Individuals who consume large quantities of alcohol on particular occasions, however otherwise consume moderate amounts of alcohol on a regular e.g., weekly basis, including binge drinkers and heavy drinkers, generally present an acute risk of injury, and/or violence and/or loss of control affecting others as well as themselves.

Exemplary chronic and acute drinking behaviors that are considered to be either harmful drinking or hazardous drinking are provided in Table 1. Equivalent alcohol intake frequencies and levels to those listed in Table 1 are obtained for any one-month period or any annual period by standard procedures and, for example, a male consuming about 1000 g or more alcohol per calendar month, or a female consuming about 800 g or more alcohol per calendar month, is a heavy drinker.

Because the alcohol contents of different types of alcoholic beverages e.g., wine, spirit, beer and ale, often vary considerably, the term "standard drink" was introduced in an attempt to standardize safe and non-safe drinking behaviors e.g., Table 2. This merely provides consumers with a conversion factor for determining a number of alcoholic beverages of a particular kind that may be consumed in a specified period of time without becoming harmful/hazardous behavior e.g., based on weight of alcohol consumption in a defined period as provided in Table 1 hereof.

The demographics of problem drinkers also suggest heterogenic groupings of individuals based on patterns of drinking, wherein the bulk of problem drinkers engage in acute harmful or hazardous drinking as opposed to having an established pattern over a longer period of time i.e., chronic problem drinking. However, all categories of problem drinker pose health and social problems. For example, a smaller section e.g., 5-10% of problem drinkers suffer multiple negative consequences of chronic harmful drinking or chronic hazardous drinking behavior, whilst a larger section e.g., 10-20% of problem drinkers suffer from a single adverse consequence such as memory loss of chronic harmful drinking or chronic hazardous drinking behavior, and an even larger proportion e.g., up to about 70-85%, of problem drinkers engage in acute problem drinking behavior with injurious results. All such classes are likely to have attempted suicide at some stage, however those suffering multiple negative consequences are more likely to suffer from a generalized anxiety disorder or mixed anxiety or depressive disorder. Excess consumption increases the risk of injury or disease almost exponentially in proportion to the frequency and/or level of alcohol consumption.

TABLE 1

Behavioral alcohol consumption index for problem drinking behaviors

| Harmful/hazardous Drinking Behavior | Alcohol intake (males) | Alcohol intake (females) |
|---|---|---|
| Chronic drinking | Equivalent of 250 grams or more alcohol consumed per day for 7 days in any one-week period or Equivalent of 490 grams or more alcohol consumed per day for 4-6 days in any one-week period or Equivalent of 240 grams or more alcohol consumed per day for 2-3 days in any one-week period or Two or more bouts of binge drinking or heavy drinking in any two-week period or Less than two alcohol-free days in any one-week period or Alcohol intake sufficient to reach a blood alcohol level of 0.05% on two or more consecutive days in any one-week period | Equivalent of 160 grams or more alcohol consumed per day for 4 days or more in any one-week period or Equivalent of 250 grams or more alcohol consumed per day for 2-3 days in any one-week period or Equivalent of 360 grams or more alcohol consumed per day for 2 or more days in any one-week period or Two or more bouts of binge drinking or heavy drinking in any two-week period or Less than two alcohol-free days in any one-week period or Alcohol intake sufficient to reach a blood alcohol level of 0.05% on two or more consecutive days in any one-week period or Any regular alcohol consumption over two or more consecutive days when pregnant or breast-feeding |
| Binge Drinking | Alcohol intake sufficient to reach a blood alcohol level of 0.08% on at least one day in a one-week period | Alcohol intake sufficient to reach a blood alcohol level of 0.08% on at least one day in a one-week period |
| Heavy Drinking | Equivalent of 250 grams of alcohol on one day in a one-week period | Equivalent of 90 grams of alcohol on one day in a one-week period |
| Other Acute Problem Drinking | Alcohol intake sufficient to reach a blood alcohol level of 0.05% on one day in a one-week period | Alcohol intake sufficient to reach a blood alcohol level of 0.05% on one day in a one-week period or Any alcohol consumption on one day when pregnant or breast-feeding |

TABLE 2

Exemplary alcohol contents of standard drinks

| Country | Mass Alcohol in Std. Drink (g) |
|---|---|
| Australia | 10 |
| Austria | 6 |
| Canada | 13.5 |
| Denmark | 12 |
| Finland | 11 |
| France | 12 |
| Hungary | 17 |
| Iceland | 9.5 |
| Ireland | 10 |
| Italy | 10 |
| Japan | 19.75 |
| Netherlands | 9.9 |

TABLE 2-continued

Exemplary alcohol contents of standard drinks

| Country | Mass Alcohol in Std. Drink (g) |
|---|---|
| New Zealand | 10 |
| Poland | 10 |
| Portugal | 14 |
| Spain | 10 |
| UK | 7.9 |
| USA | 14 |

Chronic harmful or chronic hazardous drinking behavior clearly increases the risk of developing alcohol dependence syndrome, which may also be considered a form of problem drinking. Alcohol dependence syndrome is a cluster of cognitive, behavioral, and physiological symptoms characterized by three or more of the following symptoms in a twelve-month period:
1. a strong desire or sense of compulsion to drink; and/or
2. difficulties in controlling drinking in terms of onset, termination, or levels of use; and/or
3. a physiological withdrawal state when alcohol use has ceased or been reduced, or use of alcohol to relieve or avoid withdrawal symptoms; and/or
4. evidence of tolerance, such that increased doses of alcohol are required to achieve effects originally produced by lower doses; and/or
5. progressive neglect of alternative pleasures or interests because of alcohol use; and/or
6. continued use despite clear evidence of harmful consequences.

Predictors of Problem Drinking

Widespread risk factors in early life are associated with problem drinking, and both genetic and environmental factors have been associated with the development of problem drinking.

For example, children of alcoholics are significantly more likely than children of non-alcoholics to initiate drinking during adolescence and to develop alcohol dependency, and early initiation of drinking is an important risk factor for later alcohol-related problems. Lack of parental support, monitoring, and communication have been significantly related to frequency of drinking, heavy drinking, and drunkenness among adolescents. Harsh, inconsistent discipline and hostility or rejection are also predictive of adolescent drinking and alcohol-related problems.

Child abuse and other trauma have been proposed as risk factors for subsequent alcohol problems. Adolescents in treatment for alcohol abuse or dependence reported higher rates of physical abuse, sexual abuse, violent victimization, witnessing violence, and other traumas compared with controls such that adolescents in treatment are about 6 times more likely than controls to have ever been abused physically and at least 18 times more likely to have ever been abused sexually. At least about 10% of problem drinking adolescents have experienced posttraumatic stress disorder.

Of the numerous markers associated with problem drinking in men at age 30, low birth weight, number of life crises in childhood, ratings of childhood unhappiness and antisocial personality disorder have been shown to be independent risk factors.

Peer drinking and peer acceptance of drinking are also important factors associated with problem drinking in adolescents.

Accordingly, acute hazardous drinking behavior in a subject having one or more of the foregoing risk factors may be indicative of the subject being at risk of developing problem drinking.

Current Therapies

Current therapies for harmful and/or hazardous drinking are limited to brief interventions by families, friends and health care professionals. Such brief interventions generally involve counseling to reduce alcohol consumption. Currently, there are no therapeutics having proven efficacy in preventing or treating non-dependent problem drinking, especially acute problem drinking.

Pharmaceutical therapeutics for treatment of alcohol dependence syndrome generally address alcohol withdrawal or relapse, but have no proven effect in prolonging abstinence beyond the short-medium term e.g., up to about 6 months.

For example, during detoxification, patients in primary care may be administered one or more benzodiazepines to manage withdrawal symptoms including delirium tremens, albeit for a maximum period of seven days. For patients managed in the community, chlordiazepoxide or valium is a preferred benzodiazepine for managing withdrawal symptoms. Patients suffering from Wernicke-Korsakov syndrome are administered Pabrinex over several days, ideally in an inpatient setting having adequate resuscitation facilities.

To assist in preventing relapse or prolong abstinence in subjects suffering from alcohol dependence syndrome, acamprosate may be administered to newly-detoxified dependent patients as an adjunct to psycho-social intervention. Acamprosate acts on the GABA and glutamate neurotransmitter systems and is thought to reduce symptoms of protracted abstinence such as insomnia, anxiety, restlessness, and dysphoria. Acamprosate may increase the proportion of dependent drinkers who maintain abstinence for several weeks to months, wherein about 36% of patients taking acamprosate were continuously abstinent after 6 months, compared with 23% of subjects taking a placebo.

Topiramate, a putative GABA agonist and glutamate antagonist, has been shown to increased the proportion of subjects with 28 consecutive days of abstinence or non-hazardous/harmful drinking i.e., short-term abstinence.

Naltrexone may also reduce alcohol cravings in dependent subjects, by blocking opioid receptors that are involved in the rewarding effects of drinking alcohol and the craving for alcohol. Oral naltrexone also reduces relapse during the first 3 months by about 36%, however it less effective in maintaining abstinence over the medium to long term.

Disulfuram may be administered orally, however it requires abstinence to avoid disulfuram—alcohol reaction resulting flushing, nausea, and palpitations.

Acamprosate, naltrexone, topiramate and disulfuram each have serious contraindications associated with their use, including common side effects of nausea, vomiting, decreased appetite, headache, dizziness, fatigue, anxiety, reactions at injection sites, joint pain, muscle aches or cramps, diarrhea, somnolence, dermatitis, taste perversion, anorexia and weight loss, and cognitive dysfunction. Hepatitis, liver failure and renal impairment may arise from use of naltrexone or acamprosate.

It is clear that there is a need for new drugs for the treatment and/or prevention of problem drinking, especially in non-dependent problem drinkers and for prolonging abstinence in dependent problem drinkers beyond a short term.

SUMMARY OF THE INVENTION

1. Introduction

In work leading up to the present invention the inventors sought to determine whether or not oxytocin reduces self-administration of alcohol in the P rat, an accepted animal model of problem drinking, and whether or not oxytocin promotes or enhances abstinence from alcohol in the P rat model e.g., in the medium-long term. As exemplified herein, the inventors found that male and female P rats having a preference for alcohol reduced their alcohol consumption significantly following administration of a single acute dose of oxytocin, and that alcohol-nave animals administered with repeated doses of oxytocin reduced alcohol intake and preference for alcohol. The animal model data suggest that an effective amount of oxytocin reduces self-administration of alcohol in subjects suffering from problem drinking e.g., due to a reduced alcohol preference and/or alcohol craving, and also reduces a desire for alcohol in subjects predisposed to developing problem drinking behavior.

Accordingly, the present invention provides therapeutic and prophylactic processes for chronic or acute problem drinking e.g., acute hazardous drinking or acute harmful drinking or chronic hazardous drinking or chronic harmful drinking, and the adverse effects of such problem drinking e.g., one or more alcohol-related diseases, comprising the administration of an effective amount of oxytocin or an analog or derivative thereof, or comprising the administration of an amount of an agonist or partial agonist of an oxytocin receptor sufficient to activate an oxytocin-induced pathway in a subject. The present invention also provides a therapeutic process for promoting moderate drinking behavior or enhancing abstinence from alcohol comprising the administration of an effective amount of oxytocin or an analog or derivative thereof, or comprising the administration of an amount of an agonist or partial agonist of an oxytocin receptor sufficient to activate an oxytocin-induced pathway in a subject. The present invention also provides for the use of oxytocin or an analog or derivative thereof or an agonist or partial agonist of an oxytocin receptor in the manufacture of a medicament for treatment or prevention of problem drinking and the adverse effects of problem drinking. The present invention also provides for the use of oxytocin or an analog or derivative thereof or an agonist or partial agonist of an oxytocin receptor in the manufacture of a medicament for promoting moderate drinking behavior or enhancing abstinence from alcohol.

It is understood by those skilled in therapeutics and preventive medicine that therapeutic and prophylactic processes wherein a composition of matter is administered to a subject it will generally transform a target biological molecule or step or process e.g., by changing a level of the molecule or flux through a step or process or changing the physical composition of the molecule such as by complexing with it, thereby producing a further transformation in symptoms of a subject being treated. Such therapeutic and prophylactic processes may also be performed with the aid of a machine e.g., syringe or other injection device, metered dose inhalation device etc.

The scope of the invention is apparent from the following summary of specific examples and/or detailed description of preferred examples and/or the accompanying claims.

2. Specific Examples of the Invention

One example of the present invention provides a method of treatment of problem drinking e.g., acute hazardous drinking or acute harmful drinking or chronic hazardous drinking or chronic harmful drinking, said method comprising administering to a subject an amount of a composition comprising oxytocin or an analog or derivative thereof or an oxytocin receptor agonist for a time and under conditions sufficient to reduce, inhibit or prevent alcohol consumption by the subject e.g., to a level that constitutes moderate drinking behavior or abstinence from alcohol, thereby treating the problem drinking in the subject. The subject may be a subject whose behavior constitutes acute hazardous drinking or acute harmful drinking or chronic hazardous drinking or chronic harmful drinking e.g., as set forth in Table 1 hereof. For example, the subject may be a male subject, a female subject including a female subject who is breastfeeding an infant, an adolescent, an adult of any age, a subject having no apparent alcohol dependency, or a subject suffering from alcohol dependence syndrome. The therapy of the invention reduces self-administration of alcohol and/or reduces alcohol intake and/or promotes abstinence in the medium or long term and, in subjects suffering from alcohol dependence syndrome, does not merely treat withdrawal.

In a related example, the present invention provides a method of treatment of problem drinking in a non-dependent problem drinker, said method comprising administering to a subject an amount of a composition comprising oxytocin or an analog or derivative thereof or an oxytocin receptor agonist for a time and under conditions sufficient to reduce, inhibit or prevent alcohol consumption by the non-dependent problem drinker e.g., to a level that constitutes moderate drinking behavior or abstinence from alcohol, thereby treating the problem drinking in the non-dependent problem drinker.

In another related example, the present invention provides a method of treatment of problem drinking in a non-abstinent alcohol-dependent problem drinker, said method comprising administering to a subject an amount of a composition comprising oxytocin or an analog or derivative thereof or an oxytocin receptor agonist for a time and under conditions sufficient to reduce, inhibit or prevent alcohol consumption by the non-abstinent alcohol-dependent problem drinker e.g., to a level that constitutes moderate drinking behavior or abstinence from alcohol, thereby treating the problem drinking in the alcohol-dependent problem drinker. By "non-abstinent" in this context is meant that the subject is still consuming alcohol at the commencement of treatment.

As used herein, the term "moderate drinking" means a level and/or frequency of alcohol consumption that is less than that constituting problem drinking but more than that constituting abstinence.

By "abstinence" is meant zero alcohol consumption in at least the short term e.g., for at least about one month or two months or three months or four months or five months or up to about six months for a human subject. Alternatively, abstinence may comprise zero alcohol consumption in the medium term e.g., at least about six months or seven months or eight months or nine months or ten months or eleven months or up to about twelve months for a human subject. Alternatively abstinence may comprise zero alcohol consumption in the long term e.g., at least about twelve months or at least about eighteen months or at least about two years or at least about three years or at least about four years or at least about five years for a human subject.

As used herein, the terms "inhibit" and "prevent" are not to be construed as necessarily indicating 100% inhibition or prevention of alcohol consumption by a subject. A partial inhibition or partial prevention e.g., as determined by a reduction in alcohol consumption to a pattern consistent with moderate drinking is sufficient and clearly encompassed by the terms "inhibit" and "prevent".

In another example, the present invention provides a method of promoting moderate drinking behavior in a subject, said method comprising administering an amount of a composition comprising oxytocin or an analog or derivative thereof or an oxytocin receptor agonist for a time and under conditions sufficient to produce a maximum alcohol intake by the subject constituting moderate drinking behavior.

In another example, the present invention provides a method of promoting moderate drinking behavior in a subject exhibiting problem drinking behavior e.g., acute hazardous drinking or acute harmful drinking or chronic hazardous drinking or chronic harmful drinking e.g., as set forth in Table 1 hereof, said method comprising administering an amount of a composition comprising oxytocin or an analog or derivative thereof or an oxytocin receptor agonist for a time and under conditions sufficient to reduce alcohol intake by the subject at least to a level that constitutes moderate drinking behavior.

In another example, the present invention also provides a method of promoting abstinence from alcohol in a subject exhibiting problem drinking behavior e.g., acute hazardous drinking or acute harmful drinking or chronic hazardous drinking or chronic harmful drinking e.g., as set forth in Table 1 hereof, said method comprising administering an amount of a composition comprising oxytocin or an analog or derivative thereof or an oxytocin receptor agonist for a time and under conditions sufficient to stop alcohol intake by the subject e.g., in the short term or medium term or long term, optionally without adverse withdrawal symptom(s). The subject may be a male subject, a female subject including a female subject who is breastfeeding an infant, an adolescent, an adult of any age, a subject having no apparent alcohol dependency, or a subject suffering from alcohol dependence syndrome.

In a related example, the present invention also provides a method of enhancing abstinence from alcohol in a subject in relapse from problem drinking e.g., acute hazardous drinking or acute harmful drinking or chronic hazardous drinking or chronic harmful drinking e.g., as set forth in Table 1 hereof, said method comprising administering an amount of a composition comprising oxytocin or an analog or derivative thereof or an oxytocin receptor agonist for a time and under conditions sufficient to extend abstinence from alcohol by the subject, optionally without adverse withdrawal symptom(s). For example, the subject may be a subject suffering from alcohol dependence syndrome.

As used herein, the term "adverse withdrawal symptom(s)" means one or more symptoms normally associated withdrawal from alcohol by an alcohol-dependent subject including anxiety, tremor, delirium tremens, irritability, excitability, emotional volatility, mood swing, depression, fatigue, confusion, nightmare, headache, sweating e.g., in the palms of the hands or face, nausea, vomiting, loss of appetite, insomnia, palor, palpitations, dilation of pupil(s), abnormal movements of the eyelids, fever, convulsion or black-out.

Treatment according to any of the foregoing examples may comprise single or multiple doses e.g., wherein doses are administered at regular intervals and/or irregular intervals.

Treatment may be ongoing during a period of reduced alcohol consumption or abstinence or relapse, or during part of that term e.g., wherein treatment comprises multiple doses of the composition administered at regular or irregular intervals such as preceding, during or following periods of acute or chronic risky behavior.

Alternatively, wherein treatment comprises a single dose, it will generally not be ongoing during a period of reduced alcohol consumption or abstinence or relapse.

The duration of reduced alcohol consumption or abstinence achieved by performing the invention according to any example hereof may be short term e.g., for at least about one month or two months or three months or four months or five months or up to about six months from the commencement of treatment. Alternatively, the duration of reduced alcohol consumption or abstinence from alcohol may be medium term e.g., at least about six months or seven months or eight months or nine months or ten months or eleven months or up to about twelve months from commencement of treatment. Alternatively, the duration of reduced alcohol consumption or abstinence from alcohol may be long term e.g., at least about twelve months or at least about eighteen months or at least about two years or at least about three years or at least about four years or at least about five years from commencement of treatment.

The therapeutic process(es) of the invention as described according to any example hereof may further comprise administration of at least one other composition for treatment of problem drinking in combination with oxytocin or an analog or derivative thereof or an oxytocin receptor agonist. For example the oxytocin or an analog or derivative thereof or an oxytocin receptor agonist may be administered simultaneously or successively with acamprosate, naltrexone, topiramate, disulfuram, or one or more benzodiazepines e.g., chlordiazepoxide. Such combination therapy may provide additional assistance to a subject suffering from alcohol dependence syndrome. For example, a combination of oxytocin or an analog or derivative thereof or an oxytocin receptor agonist and one or more benzodiazepines may provide assistance with symptoms of withdrawal in addition to reducing self-administration and enhancing abstinence. In another example, a combination of oxytocin or an analog or derivative thereof or an oxytocin receptor agonist and acamprosate or naltrexone or topiramate may enhance abstinence more than an individual component of the combination.

Another example of the present invention provides a method of preventing problem drinking e.g., acute hazardous drinking or acute harmful drinking or chronic hazardous drinking or chronic harmful drinking, in a subject at risk thereof, said method comprising administering an amount of a composition comprising oxytocin or an analog or derivative thereof or an oxytocin receptor agonist for a time and under conditions sufficient to prevent or delay alcohol intake by the subject e.g., alcohol intake at a level that constitutes problem drinking e.g., acute hazardous drinking or acute harmful drinking or chronic hazardous drinking or chronic harmful drinking, thereby preventing problem drinking in the subject.

As used herein, the term "delay" shall not be taken to mean an indefinite delay in alcohol intake by the subject.

A subject for preventive therapy may not exhibit any symptom of problem drinking, however may have a family history of alcohol use disorder e.g., alcoholism or alcohol misuse, that renders the subject susceptible to developing problem drinking behavior. Similarly, a subject may be exposed to an environment of acute or chronic hazardous drinking or harmful drinking that renders the subject susceptible to developing problem drinking. Alternatively, or in addition, a subject at risk of becoming a problem drinker may be a subject who had a low birth weight, especially a male. Alternatively, or in addition, a subject at risk of becoming a problem drinker may be a subject who had a number of life crises in childhood and/or was physically or sexually abused in childhood, especially a male. Alternatively, or in addition, a subject at risk of becoming a problem drinker may be a subject who suffered childhood unhappiness, especially a male. Alternatively, or in addition, a subject at risk of becoming a problem drinker may be a subject who was characterized as having an antisocial personality disorder in childhood, especially a male.

The risk of any subject(s) developing chronic problem drinking behavior, including a subject referred to in the preceding paragraph, is enhanced if the subject is already an acute problem drinker such as a binge drinker or heavy drinker.

It is to be understood that a subject for preventive therapy need not be an abstainer from alcohol consumption and may be a moderate drinker. Alternatively, or in addition, a subject at risk of becoming a problem drinker may be a subject who has a history of hazardous drinking or harmful drinking, whether acute or chronic, however is in a period of relapse from such condition(s).

Prophylactic treatment may comprise single or multiple doses of the composition e.g., wherein doses are administered at regular intervals and/or irregular intervals.

Prophylactic treatment may be ongoing during a period of risk e.g., exposure to one or more environmental factors or stressors that trigger or promote problem drinking behavior in the subject. In the case of a subject having a genetic predisposition to alcohol use disorder e.g., alcohol dependent syndrome, treatment may be long term treatment comprising therapy for one or more years.

In the foregoing examples of the invention, the administered composition may comprise an amount of oxytocin or an analog or derivative thereof or an agonist or partial agonist of an oxytocin receptor sufficient to stimulate oxytocin reception and/or downstream signaling from oxytocin receptors in vivo when administered to a subject in need thereof. In such an example, the effective dose of the active agent i.e., that crosses the blood-brain barrier of the subject to thereby exert an effect, may be low. That is, the administered composition may be suitable for enhancing endogenous oxytocin production by the subject. Alternatively, the administered composition may comprise an amount of oxytocin or an analog or derivative thereof or an agonist or partial agonist of an oxytocin receptor sufficient to exert an effect without a need for endogenous oxytocin production when administered to a subject in need thereof. That is, the administered composition may be suitable for enhancing oxytocin reception and/or downstream signaling from oxytocin receptors in vivo.

There are various modes of administering a composition in accordance with a method of the present invention for the purposes of therapy or prophylaxis of problem drinking. In one example, the composition is administered orally e.g., as capsules, soft gels, or tablets; powders or granules; solutions or suspensions in aqueous or non-aqueous liquids; edible foams or whips; or oil-in-water liquid emulsions or water-in-oil liquid emulsions. In another example, the composition is administered by injection or infusion e.g., intravenous, intraperitoneal, intracerebral, subcutaneous, intramuscular, intraocular, intraarterial, intracerebrospinal, intralesional injection. In another example, the composition is administered by inhalation e.g., intranasally or by pulmonary spray. For example, the composition can be solubilized and loaded into a suitable dispenser for administration (e.g., an atomizer, nebulizer or pressurized aerosol dispenser). In another example, the composition is administered topically e.g., by means of a transdermal patch. The composition will generally be formulated with a suitable excipient, carrier or diluent for administration to a subject e.g., using an alcohol-containing solution or detergent-containing solution to enhance solubility of the active agent i.e., the oxytocin or an analog or derivative thereof or an agonist or partial agonist of an oxytocin receptor. A suitable detergent is a non-ionic detergent. A suitable alcohol is ethanol, isopropanol or butanol.

Preferred modes of administration permit or facilitate sufficient amount of oxytocin or an analog or derivative thereof or an agonist or partial agonist of an oxytocin receptor to cross the blood-brain barrier e.g., to stimulate oxytocin production or oxytocin reception and downstream signaling from oxytocin receptors.

In these examples of therapeutic and preventive intervention, the method may additionally comprise disrupting or perforating the blood-brain barrier to thereby permit the composition to cross the blood brain barrier and then administering the composition e.g., in the case of a composition that is not readily able to cross the blood brain barrier when administered at a remote location from the central nervous system. In one example, a focused ultrasound is applied to a region of the blood brain barrier, to thereby permit a composition to cross the blood brain barrier and then administering the composition e.g., by injection or infusion. Preferably, such disruption or perforation of the blood-brain barrier is temporary and for a minimum time and sufficient for administration of the composition to occur.

In another example, the present invention provides ex vivo indications for a composition comprising an amount of oxytocin or an analog or derivative thereof or an agonist or partial agonist of an oxytocin receptor in the treatment and prevention of problem drinking e.g., acute hazardous drinking or acute harmful drinking or chronic hazardous drinking or chronic harmful drinking, and/or in the treatment of one or more alcohol use disorders and/or in the treatment of the adverse effects of problem drinking e.g., one or more alcohol-related diseases. For example, the present invention provides a composition comprising oxytocin or an analog or derivative thereof or an agonist or partial agonist of an oxytocin receptor for use in a method of therapy of the human body for reducing problem drinking in a subject. For example, the present invention provides a composition comprising oxytocin or an analog or derivative thereof or an agonist or partial agonist of an oxytocin receptor for use in a method of therapy of the human body for preventing problem drinking in a subject at risk thereof. For example, the present invention provides a composition comprising oxytocin or an analog or derivative thereof or an agonist or partial agonist of an oxytocin receptor for use in a method of therapy of the human body for enhancing abstinence from alcohol in a subject in relapse from problem drinking. For example, the present invention provides a composition comprising oxytocin or an analog or derivative thereof or an agonist or partial agonist of an oxytocin receptor for use in a method of therapy of the human body for promoting abstinence from alcohol in a subject exhibiting problem drinking behavior. For example, the present invention provides a composition comprising oxytocin or an analog or derivative thereof or an agonist or partial agonist of an oxytocin receptor for use in a method of therapy of the human body for promoting moderate drinking behavior in a subject exhibiting problem drinking behavior.

In a related example, the present invention provides for a use of oxytocin or an analog or derivative thereof or an agonist or partial agonist of an oxytocin receptor in the manufacture of a medicament for therapy of the human body for alcohol-related conditions e.g., in the treatment or prevention of problem drinking in a subject e.g., acute hazardous drinking or acute harmful drinking or chronic hazardous drinking or chronic harmful drinking and/or in the treatment of one or more alcohol use disorders and/or in the treatment of the adverse effects of problem drinking e.g., one or more alcohol-related diseases. The present invention also provides for a use of oxytocin or an analog or derivative thereof or an agonist or partial agonist of an oxytocin receptor in the manufacture of a medicament for promoting or enhancing abstinence from alcohol in a subject e.g., a problem drinker or subject in relapse from problem drinking. The present invention also provides for a use of oxytocin or an analog or derivative thereof or an agonist or partial agonist of an oxytocin receptor in the manufacture of a medicament for promoting moderate drinking behavior in a subject exhibiting problem drinking behavior or at risk of problem drinking. A medicament prepared in accordance with the present invention may be formulated for oral administration to a subject or for administration to a subject by injection or for administration to a subject by inhalation. Formulations for other modes of administration are not excluded.

The medicament may be formulated such that the level of active agent such oxytocin or an analog or derivative thereof or an agonist or partial agonist of an oxytocin receptor crossing the blood-brain barrier is sufficient to provide a beneficial effect in terms of reducing drinking as determined by enhanced alcohol-free days per week and/or reduced alcohol intake per day and/or reduced bouts of heavy drinking or harmful drinking or hazardous drinking by the subject when administered in a single dose or a plurality of doses. Alternatively, or in addition, the medicament may be formulated such that the level of active agent such as oxytocin or an analog or derivative thereof or an agonist or partial agonist of an oxytocin receptor is sufficient to enhance endogenous oxytocin production by a subject receiving one or more dosage units of the medicament e.g., in a feed-forward mechanism. Alternatively, or in addition, the medicament may be formulated such that the level of active agent such as oxytocin or an analog or derivative thereof or an agonist or partial agonist of an oxytocin receptor is sufficient to enhance oxytocin reception and/or downstream signaling in the subject.

Another example of the present invention provides a method of identifying a compound for the treatment or prophylaxis of problem drinking e.g., acute hazardous drinking or acute harmful drinking or chronic hazardous drinking or chronic harmful drinking, and/or for the treatment of one or more alcohol use disorders and/or for the treatment of the adverse effects of problem drinking e.g., one or more alcohol-related diseases, said method comprising selecting an oxytocin analog or derivative or an agonist or partial agonist of an oxytocin receptor that reduces problem drinking in a subject to a level obtained using an equimolar concentration of oxytocin e.g., as determined by enhanced alcohol-free days per week and/or reduced alcohol intake per day and/or reduced bouts of harmful drinking or hazardous drinking by the subject when administered in a single dose or a plurality of doses. The method may further comprise e.g., as a first step, determining a reduction in problem drinking in the presence and absence of the oxytocin analog or derivative or an agonist or partial agonist of an oxytocin receptor and, optionally, in the presence and absence of oxytocin e.g., an equimolar concentration of oxytocin. Alternatively, or in addition, the method may further comprise e.g., as a first step, providing an oxytocin analog or derivative or an agonist or partial agonist of an oxytocin receptor to a subject. Alternatively, or in addition, the method may further comprise e.g., as a first step, obtaining an oxytocin analog or derivative or an agonist or partial agonist of an oxytocin receptor.

In a related example, the present invention also provides a method for screening a library of compounds or a mixture of compounds for identifying or isolating a compound for the treatment or prophylaxis of problem drinking e.g., hazardous drinking and/or harmful drinking and/or for the treatment of one or more alcohol use disorders and/or for the treatment of the adverse effects of problem drinking e.g., one or more alcohol-related diseases, said method comprising:

(i) obtaining a mixture of compounds or a library comprising compounds comprising an oxytocin analog or derivative or an agonist or partial agonist of an oxytocin receptor;
(ii) administering the mixture at (i) or one or more compounds of the mixture at (i) to a subject suffering from problem drinking or at risk of developing problem drinking behavior;
(iii) determining the ability of said mixture or said one or more compounds at administered at (ii) to reduce, inhibit, prevent or delay problem drinking in the subject e.g., as determined by enhanced alcohol-free days per week and/or reduced alcohol intake per day and/or reduced bouts of heavy drinking or harmful drinking or hazardous drinking by the subject when administered in a single dose or a plurality of doses; and
(iv) selecting one or more compounds from the mixture or compounds administered at (i) that reduce(s), inhibit(s), prevent(s) or delay(s) problem drinking in the subject e.g., by repeating (ii) and (iii) on an aliquot of the mixture or one or more compounds, thereby identifying or isolating a compound for the treatment or prevention of problem drinking.

In accordance with the foregoing example, determination of the ability of the compound to reduce, inhibit, delay or prevent problem drinking may comprise comparing alcohol-free days per week and/or reduced alcohol intake per day and/or bouts of heavy drinking or harmful drinking or hazardous drinking by a subject treated with the mixture or plurality relative to alcohol-free days per week and/or reduced alcohol intake per day and/or bouts of heavy drinking or harmful drinking or hazardous drinking by a subject treated with oxytocin e.g., an equimolar concentration of oxytocin and/or relative to alcohol-free days per week and/or reduced alcohol intake per day and/or bouts of heavy drinking or harmful drinking or hazardous drinking by a subject treated with placebo or an untreated subject.

Another example of the present invention provides a process for isolating a composition for the treatment or prophylaxis of problem drinking, said process comprising performing a method according to any example hereof to thereby identify a compound for the treatment or prophylaxis of problem drinking and isolating the identified oxytocin analog or derivative or an agonist or partial agonist of an oxytocin receptor e.g., from a mixture of compounds or a library of compounds. A mixture of compounds may comprise a natural product e.g., in a plant or tissue extract thereof, in an animal tissue or extract thereof, or a mixture may comprise a synthetic compound e.g., in a mixture of other synthetic or natural compounds not having the desired activity.

In the case of a library of compounds displayed separately wherein each compound is substantially pure prior to performance of the method, such isolation results in the separation of the compound from other compounds in the library that do not have the requisite activity. In this case, the term "separating" extends to determining the activity of one library component relative to another library component and selecting a compound having the desired activity.

The term "separation" in this context refers to the use of any chemical or biochemical purification process known in the art to fractionate the mixture of plurality of compounds coupled with assaying the fractions produced for activity with respect to, reducing, inhibiting, preventing or delaying problem drinking and selecting fractions having one or more of said activities.

The term "separation" in this context also refers to a process comprising iterated use of any chemical or biochemical purification process known in the art to partially or completely purify a compound from a mixture of plurality of compounds and assaying the fractions produced in each iteration of the process for activity with respect to reducing, inhibiting, preventing or delaying problem drinking, and selecting at each iteration one or more fractions having one or more of said activities. A process may be repeated for n iterations wherein n is sufficient number of iterations to reach a desired purity of the compound e.g., 50% or 60% or 70% or 80% or 90% or 95% or 99%. e.g., wherein n is an integer from zero to about ten. As is known to the skilled artisan, such iterations do not require iteration of precisely the same purification processes and more generally utilize different processes or purification conditions for each iteration.

The foregoing examples of methods and processes for identifying or isolating therapeutic/prophylactic compounds may additionally comprise:

(v) optionally, determining the structure of the compound;
(vi) optionally, providing the name or structure of the compound; and
(vii) providing the compound.

It is to be understood that an identified or isolated compound in substantially pure form i.e., free from contaminants that might cause adverse side effects or contraindications or antagonize the activity of the active compound, can be formulated into a medicament suitable for treatment and/or prophylaxis of problem drinking The present invention clearly extends to the direct product of any method of identification or isolation of a therapeutic compound described herein. Accordingly, another example of the present invention provides a composition for the treatment or prophylaxis of problem drinking wherein said composition comprises an oxytocin analog or derivative or an agonist or partial agonist of an oxytocin receptor isolated by the process according to any example hereof.

Another example of the present invention provides a process for producing a composition for the treatment or prophylaxis of problem drinking, said process comprising performing a method according to any example hereof to thereby identify a compound for the treatment or prophylaxis of problem drinking and synthesizing an identified oxytocin analog or derivative or an agonist or partial agonist of an oxytocin receptor. Standard chemical syntheses are employed.

Another example of the present invention provides a process for producing a composition for the treatment or prophylaxis of problem drinking, said method comprising performing a method according to any example hereof to thereby identify a compound for the treatment or prophylaxis of problem drinking and formulating an oxytocin analog or derivative or an agonist or partial agonist of an oxytocin receptor for administration to a subject suffering from problem drinking or at risk of suffering from problem drinking.

The present invention also provides a method of treatment or prophylaxis comprising:

(i) identifying a problem drinker or at risk of developing problem drinking;
(ii) obtaining a formulation comprising an oxytocin analog or derivative or an agonist or partial agonist of an oxytocin receptor according to any example hereof; and
(iii) administering said formulation to said subject for a time and under conditions sufficient to modify drinking behavior in the subject or recommending such administration to a subject.

2. Definitions

This specification contains nucleotide and amino acid sequence information prepared using PatentIn Version 3.5, presented herein after the claims. Each nucleotide sequence is identified in the sequence listing by the numeric indicator <210> followed by the sequence identifier (e.g. <210>1, <210>2, <210>3, etc). The length and type of sequence (DNA, protein (PRT), etc), and source organism for each nucleotide sequence, are indicated by information provided in the numeric indicator fields <211>, <212> and <213>, respectively. Nucleotide sequences referred to in the specification are defined by the term "SEQ ID NO:" followed by the sequence identifier (e.g. SEQ ID NO: 1 refers to the sequence in the sequence listing designated as <400>1).

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", is understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each example described herein is to be applied mutatis mutandis to each and every other example unless specifically stated otherwise.

Each definition or clarifying term described herein shall be taken to apply mutatis mutandis to each and every example of the invention unless the context requires otherwise.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific examples described herein, which are intended for the purpose of exemplification only. Functionally-equivalent products, compositions and methods are clearly within the scope of the invention, as described herein.

DETAILED DESCRIPTION OF THE PREFERRED EXAMPLES

Figure 1:
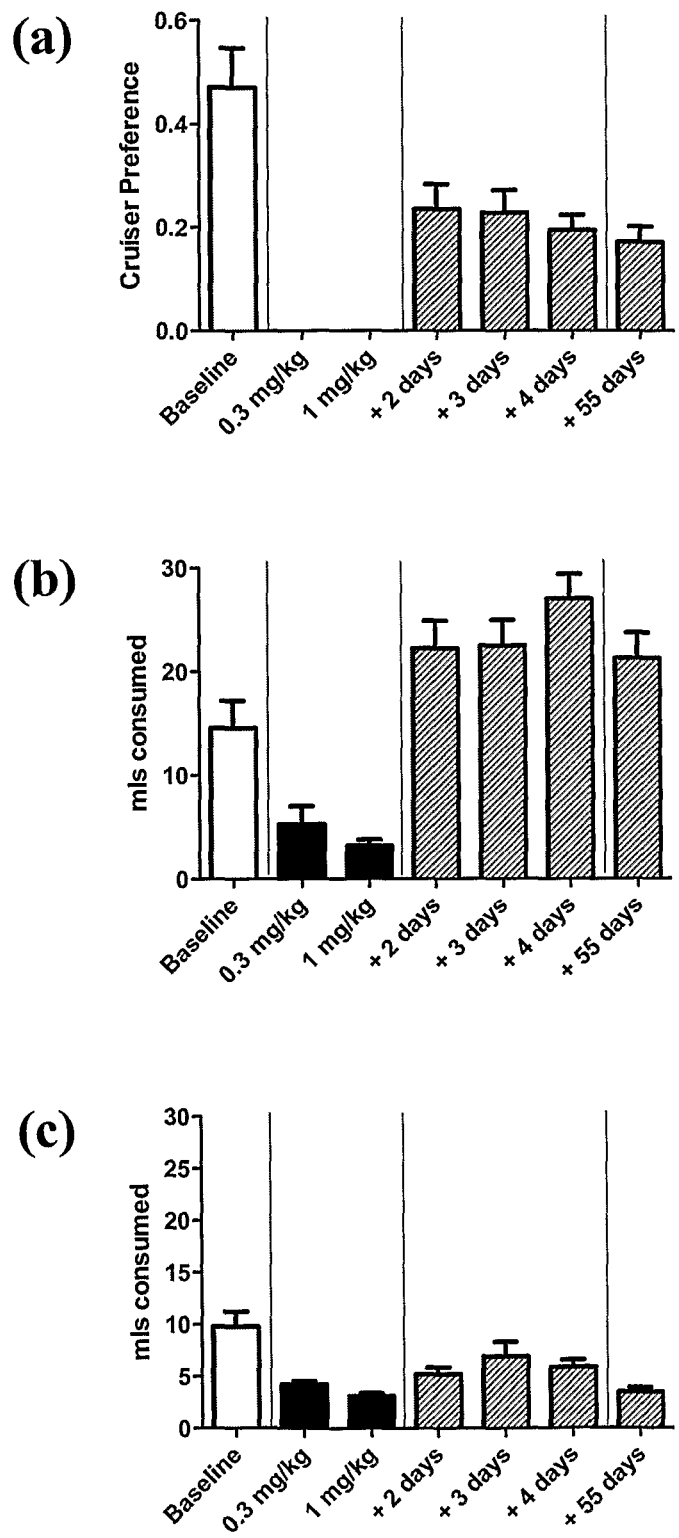
FIG. 1 provides a graphical representation showing: (a) preference of male and female P rats for Vodka Cruiser compared to 3% (w/v) sucrose solution in the absence of oxytocin (baseline), immediately after challenge with 0.3 and 1 mg/kg oxytocin, and 2, 3, 4, and 55 days after administration of 1 mg/kg oxytocin; (b) intake of sucrose by male and female P rats in the absence of oxytocin (baseline), immediately after challenge with 0.3 and 1 mg/kg oxytocin, and 2, 3, 4, and 55 days after administration of 1 mg/kg oxytocin; and (c) intake of Vodka Cruiser by male and female P rats in the absence of oxytocin (baseline), immediately after challenge with 0.3 and 1 mg/kg oxytocin, and at 2, 3, 4, and 55 days after administration of 1 mg/kg oxytocin. Data are for a representative sample of n=8 male and n=8 female P rats. Data indicate a robust baseline alcohol intake in untreated males and females, which was reduced by about 50% in both sexes 2 days following treatment, indicating reduced preference for alcohol in treated animals. The reduction in alcohol preference and alcohol intake by P rats was sustained for at least about 7-8 weeks in this animal model, which is considered medium-tolong term in rats. The reduction in alcohol consumption was comparable between the sexes.

Oxytocin and Analogs and Derivatives Thereof and Oxytocin Receptor Agonists

In one example, of the present invention, an oxytocin peptide is employed. As used herein, the term "oxytocin" means any peptide comprising the sequence:

(SEQ ID NO: 1)
Cys-Tyr-Ile-Gln-Asn-Cys-Pro-Leu-Gly;

or a synthetic variant of said peptide wherein amino group is removed from the N-terminus and/or added to the C-terminus e.g., using Fmoc peptide synthesis. For example, the term "oxytocin" shall be taken to include one or more of native oxytocin peptide, 9-amido-oxytocin, and 1-hydroxy-deaminooxytocin.

In another example of the invention, a peptidyl derivative of oxytocin is employed. As used herein the term "derivative" shall be taken to mean a peptide that is derived from oxytocin e.g., a fragment or processed form of the peptide. For example, an oxytocin derivative may comprise 6 or 7 or 8 or 9 contiguous amino acid residues of SEQ ID NO: 1.

The term "derivative" also encompasses fusion proteins comprising an oxytocin peptide of the invention. For example, the fusion protein comprises a label, such as, for example, an epitope, e.g., a FLAG epitope or a V5 epitope or an HA epitope, or a protein transduction domain, or one or more linker moieties. For example, a FLAG epitope is useful for inclusion in a fusion peptide comprising oxytocin or an analog or derivative thereof or an agonist of an oxytocin receptor to facilitate detection and/or purification of the fusion. Alternatively, or in addition, to facilitate peptide entry of a peptide comprising oxytocin or an analog or derivative thereof or an agonist of an oxytocin receptor into a cell, the peptide may be conjugated to (e.g., expressed as a fusion with) a protein transduction domain e.g., the TAT sequence from HIV or the Penetratin sequence derived from the Antennapedia homeodomain protein such as described by Temsamani and Vidal, *Drug Discovery Today* 9: 1012-1019 (2004); Zhao and Weisledder *Medicinal Research Reviews,* 24: 1-12 (2004) or Wagstaff and Jans, *Current Medicinal Chemistry,* 13: 1371-1387 (2006). Alternatively, or in addition, a peptidyl moiety of a fusion peptide comprising one or more oxytocin molecules, analogs or derivatives may be separated from another peptidyl moiety of the fusion, e.g., another oxytocin molecule or an analog or derivative of oxytocin or a protein transduction domain or epitope, by a linker that facilitates the independent folding of the linked moieties e.g., a linker comprising poly-glycine or poly-serine or a mixture of glycine and serine residues.

The term "derivative" also encompasses an oxytocin peptide modified to contain one or more-chemical moieties other than an amino acid e.g., linked covalently to an amino terminal amino acid residue, a carboxy terminal amino acid residue, or an internal amino acid residue of oxytocin. Such modifications include the addition of a protective or capping group on a reactive moiety in the peptide, addition of a detectable label, amidation or esterification of one or more residues of the peptide, or other changes that do not ablate or destroy the activity of the oxytocin peptide. For example, esterification or amidation e.g., at the N-terminus or C-terminus, may facilitate cyclization of an oxytocin derivative.

In another example, a peptide derivative of oxytocin has the functionality of an oxytocin peptide or derivative thereof. By "functionality" is meant that the derivative possesses the same qualitative activity as a native oxytocin or derivative from which it was derived. It is to be understood that an oxytocin derivative need not possess the same activity or enhanced activity relative to a native oxytocin from which it was derived. For example, a derivative of oxytocin may possess reduced affinity for an oxytocin receptor compared to native oxytocin, however possess enhanced stability following administration to a subject in need thereof. For the purpose of clarifying such functionality, an oxytocin peptide is capable of forming an association with a neurophysin 1 polypeptide in vitro, in situ, or in vivo. By "association" is meant a dimer or high-order complex, e.g., wherein the binding partners interact non-covalently such as by van der Waals forces. Alternatively, or in addition, an oxytocin peptide is capable of binding to an oxytocin receptor in vitro or in situ, or in vivo in one or more systems, organs, tissues or cells of the human body, for example: one or more systems selected from olfactory system, central nervous system, peripheral nervous system, limbic system, reproductive system, cardiovascular system and neuro-endocrine system; and/or one or more organs selected from ovary, testis, uterus, adrenal gland, liver, mammary gland, brain, brain stem, spinal cord, nasal cavity, and/or one or more tissues selected from basal ganglia, thalamus, hypothalamus e.g., ventromedial hypothalamus, ventromedial hypothalamic nucleus, supraoptic nucleus, paraventricular nucleus, lateral septal nucleus, basal nuclei of Meynert, basolateral amygdaloid nucleus, stria terminalis (BSNT), central amygdaloid nucleus, ventral subiculum olfactory bulb, olfactory nucleus, myometrium and endometrium; and/or one or more cells selected from epithelial cells, adipocytes and neurons e.g., found in or derived from one or more of tissues, organs or systems described herein. Alternatively, or in addition, an oxytocin peptide is capable of stimulating production of oxytocin in one or more systems, organs, tissues or cells of the human body (i.e., in vivo) e.g., by means of a feed-forward mechanism, to thereby amplify a therapeutic result obtained from a low dosage of oxytocin at an effector site. By "effector site" is meant an organ, tissue or cell of the human body at which oxytocin exerts a biological effect. For example, a low concentration of oxytocin crossing the blood-brain barrier following administration of one or more dosage units of oxytocin may enhance synthesis of oxytocin in the supraoptic nucleus and/or paraventricular nucleus, thereby enhancing the stimulation of oxytocin receptors at the effector site(s) e.g., in the central nervous system or olfactory system. A preferred functional derivative of oxytocin for use in the present invention is at least capable of binding to an oxytocin receptor in vitro or in situ, or in vivo and eliciting signal transduction e.g., via a phosphatidylinositol-calcium second messenger system, to thereby mimic oxytocin function.

In another example of the invention, a peptide analog of oxytocin is employed. As used herein, the term "analog" shall be taken to mean an oxytocin peptide or derivative thereof that is modified to comprise one or more naturally-occurring and/ or non-naturally-occurring amino acids, generally without ablation or destruction of the activity of the oxytocin peptide or derivative. As with derivatives, analogs need not possess the same activity or enhanced activity relative to native oxytocin or a derivative thereof from which it was derived.

In one example, a peptide analog comprising one or more conservative amino acid substitutions relative to native oxytocin or a derivative thereof is employed in the present invention. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). In accordance with this example, a suitable analog of oxytocin may comprise the following amino acids at each position of the peptide:

Position 1: glycine, asparagine, glutamine, serine, threonine, or tyrosine;
Position 2: glycine, asparagine, glutamine, serine, threonine, or cysteine;
Position 3: alanine, valine, leucine, proline, methionine, tryptophan;
Position 4: glycine, asparagine, serine, threonine, tyrosine, cysteine;
Position 5: glycine, glutamine, serine, threonine, tyrosine, cysteine;
Position 6: glycine, asparagine, glutamine, serine, threonine, tyrosine;
Position 7: alanine, valine, leucine, isoleucine, phenylalanine, methionine, tryptophan;
Position 8: alanine, valine, isoleucine, proline, phenylalanine, methionine, tryptophan;
Position 9: asparagine, glutamine, serine, threonine, tyrosine, cysteine.

In another example, an analog of oxytocin or an oxytocin derivative comprises a conservative amino acid substitution as defined at position 3 and/or position 5 and/or position 8 relative to SEQ ID NO: 1 e.g., Gln5Thr or Gln5Ser alone or in combination with Leu8Ile and/or Ile3Phe. For example, the analog may be 4-serine, 8-isoleucine-oxytocin or oxypressin i.e., 3-phenylalanine-oxytocin.

In another example, an analog of oxytocin or oxytocin derivative comprises cysteine-1 and/or cysteine-6 and/or leucine-7 of native oxytocin. For example, the analog may be selected from the group consisting of: 4-threonine-1-hydroxy-deaminooxytocin; 4-serine, 8-isoleucine-oxytocin; 9-deamidooxytocin; 7-D-proline-oxytocin; (2,4-diisoleucine)-oxytocin; carbetocin e.g., Manning et al., Prog. Brain Res. 170: 473-512 (2005); 4-threonine, 7-glycine-oxytocin (TG-OT); oxypressin; and deamino-6-carba-oxytoxin (dC60), all of which retain Cys-1 and/or Cys-6 and/or Leu-8.

In another example, a peptide analog comprising one or more non-conservative amino acid substitutions relative to native oxytocin or a derivative thereof is employed in the present invention. A "non-conservative amino acid substitution" is one in which the amino acid residue is replaced with an amino acid residue having a dissimilar side chain or a non-naturally occurring amino acid. For example, tyrosine at position 2 and/or glutamine at position 4 of oxytocin may be substituted for a residue having a nonpolar side chain e.g., alanine, valine, leucine, isoleucine, proline, phenylalanine, methionine, tryptophan, and especially wherein Tyr-2 and/or Glu-4 is/are substituted for Ile as in 8-isoleucine-oxytocin or 4-serine, 8-isoleucine-oxytocin or (2,4-diisoleucine)-oxytocin. In another example, proline at position 7 and/or leucine at position 8 of oxytocin may be substituted for a residue having an uncharged polar side chain e.g., glycine, asparagine, glutamine, serine, threonine, tyrosine, cysteine, and especially wherein Pro-7 is substituted for Gly as in 7-glycine-oxytocin or 4-threonine, 7-glycine-oxytocin (TG-OT).

In another example, a peptide analog comprising one or more non-naturally occurring amino acids relative to native oxytocin or a derivative thereof is employed in the present invention. For example, the oxytocin or derivative thereof may be modified by substituting one or more amino acids of the native peptide sequence for one or more synthetic L-amino acids or D-enantiomers of an amino acid. For example, an analog may comprise one or more D-amino acids. D-amino acids may be produced from any amino acid having a chiral center e.g., any of the natural amino acids other than glycine. Analogs comprising such D-amino acids are generally more resistant to proteolytic breakdown and/or have longer half life than peptides comprising L amino acids and, as a consequence, may be more suitable for therapeutic intervention. For example, the analog 7-D-proline-oxytocin comprises D-proline at position 7 instead of L-proline present in the native oxytocin molecule. In addition to D amino acids, non-natural amino acids may be selected from the group consisting of hydroxyproline, β-alanine, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylananine 3-benzothienyl alanine 4-chlorophenyl alanine, 2-fluorophenylalanine, 3-fluorophenylalanine, 4-fluorophenylalanine, penicillamine, 1,2,3,4-tetrahydro-tic isoquinoline-3-carboxylic acid β-2-thienylalanine, methionine sulfoxide, homoarginine, N-acetyl lysine, 2,4-diamino butyric acid, ρ-aminophenylalanine, N-methylvaline, homocysteine, homoserine, ε-amino hexanoic acid, δ-amino valeric acid, 2,3-diaminobutyric acid. Other amino acid residues that are useful for making peptide analogs described herein can be found, e.g., in Fasman, 1989, CRC Practical Handbook of Biochemistry and Molecular Biology, CRC Press, Inc., and the references cited therein.

In another example, a peptide analog of oxytocin or a derivative thereof is a retro-peptide analog e.g., as described by Goodman et al., Accounts of Chemical Research, 12:1-7 (1979). A retro-peptide analog comprises a reversed amino acid sequence of oxytocin or a derivative thereof according to any example hereof.

In another example, a peptide analog of oxytocin or a derivative thereof is a retro-inverso peptide e.g., as described by Sela and Zisman, FASEB J. 11: 449 (1997). Retro-inverso peptide analogs are isomers of linear peptides in which the direction of the amino acid sequence is reversed (retro) and the chirality, D- or L-, of one or more amino acids therein is inverted (inverso) e.g., using D-amino acids rather than L-amino acids e.g., Jameson et al., Nature, 368, 744-746 (1994); Brady et al., Nature, 368, 692-693 (1994). The net result of combining D-enantiomers and reverse synthesis is that the positions of carbonyl and amino groups in each amide bond are exchanged, while the position of the side-chain groups at each alpha carbon is preserved. An advantage of retro-inverso peptides is their enhanced resistance to proteolytic degradation, i.e., the peptide has enhanced stability e.g., Chorev et al., Trends Biotech. 13, 438-445 (1995). Retro-inverso peptide analogs may be complete or partial. Complete retro-inverso peptides are those in which a complete sequence of oxytocin or a derivative thereof is reversed and the chirality of each amino acid other than glycine-9 is modified by substitution of L-amino acids for D-amino acids. Partial retro-inverso peptide analogs are those in which only some of the peptide bonds are reversed and the chirality of only those amino acid residues in the reversed portion is inverted. For example, one or two or three or four or five or six or seven or eight amino acid residues are D-amino acids. In another example, a peptide analog of oxytocin or a derivative thereof comprises an N-terminal substitution and/or C-terminal substitution and/or internal substitution of an amino acid in oxytocin, or a derivative thereof, for a non-amino organic acid e.g., butanoic acid. To produce such an analog, solid-phase peptide synthesis is employed wherein the invariant residue(s) is/are protected using standard Fmoc chemistry to protect Nα groups during synthesis and/or a triphenylmethyl group to protect cysteinyl sulfhydryl residue(s) during synthesis, and 1-chloro-butanoic acid is introduced at the desired location(s) in place of the native residue(s) to be substituted, and the synthesized peptide is cleaved from the solid support by standard procedures e.g., using trifluoracetic acid. For example, a peptide analog of oxytocin or a derivative thereof may be carbetocin (dCOMOT) i.e., 1-deamino-1-mono-carba-[2-O-methyltyrosine]-oxytocin, or deamino-6-carba-oxytoxin (dC60) i.e., 1-deamino-6-monocarba-[2-O-methyltyrosine]-oxytocin or deamino-di-carba-oxytocin i.e., 1-deamino-1,6-dicarba-[2-O-methyltyrosine]-oxytocin.

In another example, a peptide analog of oxytocin or a derivative thereof is a cyclic peptide. Cyclic peptides may provide enhanced binding to the oxytocin receptor e.g., a higher affinity of binding that the corresponding non-cyclized oxytocin peptide, analog or derivative. Alternatively, or in addition, cyclic peptides may be more resistant to proteolysis and, as a consequence, have longer half-lives than their linear counterparts. Cyclization may be via intramolecular bond formation i.e., between residues of the primary sequence of a molecule of oxytocin or between residues of the primary sequence of a molecule of an analog or derivative of oxytocin. For example, two cysteine residues e.g., between positions 1 and 6, of a single oxytocin molecule are capable of forming a disulfide bridge thereby cyclizing the oxytocin peptide. Similarly, derivatives or analogs of oxytocin that retain these cysteine residues may form intramolecular bonds by this mechanism. Alternatively, N-ethyldiisopropylamine (DIEA) may be employed to produce cyclic forms of deamino-carba analogs of oxytocin, e.g., carbetocin or deamino-6-carba-oxytoxin or deamino-di-carba-oxytocin. Exemplary cyclic oxytocin peptides, derivative and analogs are selected from the group consisting of:

1. oxytocin:

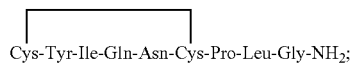

2. 4-threonine-1-hydroxy-deaminoocytocin:

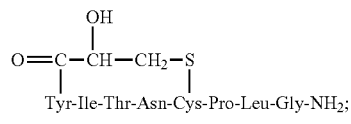

3. 4-serine, 8-isoleucine-oxytocin:

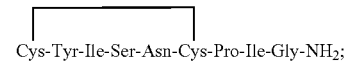

4. 9-deamidooxytocin:

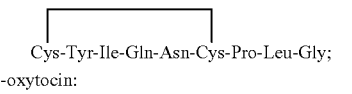

5. 7-D-proline-oxytocin:

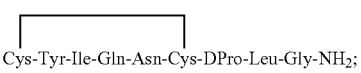

6. (2,4-diisoleucine)-oxytocin:

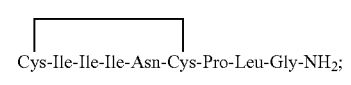

7. 4-threonine, 7-glycine-oxytocin (TG-OT):

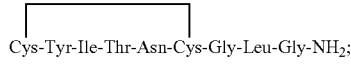

8. 3-phenylalanine-oxytocin (oxypressin):

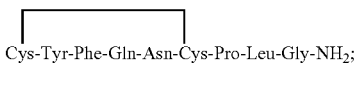

9. carbetocin:

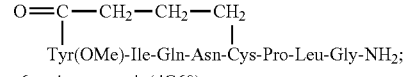

10. deamino-6-carba-oxytoxin(dC60):

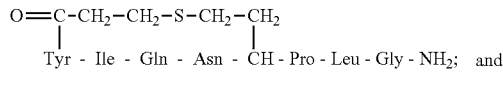   and 11. deamino-di-carba-oxytoxin:

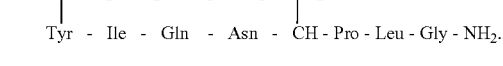

In another example, a peptide analog of oxytocin or a derivative thereof is a peptidomimetic e.g., a peptide analog that is sterically similar to oxytocin albeit comprising a sequence having an unrelated amino acid sequence. By "unrelated" is meant an amino acid sequence for which fewer amino acids are conserved relative to SEQ ID NO: 1 than would be expected at random. For example, a peptidomimetic may comprise a sequence that is less than about 20% or 30% or 40% or 50% identical to SEQ ID NO: 1. Means for producing such peptidomimetics are known in the art e.g., U.S. Pat. No. 7,270,969 to Phylogica Limited. In another example, the peptidomimetic is an isostere of oxytocin or oxytocin derivative, wherein the peptide backbone of oxytocin or a peptidyl derivative thereof has been modified e.g., a modification of the amido nitrogen, α-carbon or amide carbonyl group, or a replacement of an amide bond, or an extension of the peptidyl backbone, deletion of part of the peptidyl backbone, or backbone cross-linking e.g., to produce lactams and other cyclic structures. Peptide backbone modifications are known, including $\psi[CH_2S]$, $\psi[CH_2NH]$, $\psi[CSNH_2]$, $\psi[NHCO]$, $\psi[COCH_2]$, $\psi[(E)$ or $(Z)$ $CH=CH]$, or $\psi[CONR]$, wherein $\psi$ indicates the absence of an amide bond and wherein the structure replacing the amide group is specified within the brackets.

In another example, a peptide analog of oxytocin or a derivative thereof is a C-terminal hydroxymethyl derivative, O-modified derivative e.g., C-terminal hydroxymethyl benzyl ether, or an N-terminally modified derivative e.g., a substituted amide such as an alkylamide or hydrazide.

In another example, an analog of oxytocin or oxytocin derivative has the functionality of an oxytocin peptide or derivative thereof. By "functionality" is meant that the analog possesses the same qualitative activity as a native oxytocin or derivative from which it was derived e.g., as described herein above. A preferred functional analog for use in the present invention is at least capable of binding to an oxytocin receptor in vitro or in situ, or in vivo and eliciting signal transduction e.g., via a phosphatidylinositol-calcium second messenger system, to thereby mimic oxytocin function.

In another example of the present invention an agonist of an oxytocin receptor e.g., a selective agonist of the oxytocin receptor, is employed. As used herein, the term "agonist" refers to an agent e.g., a ligand of an oxytocin receptor, that by virtue of binding to the receptor activates it so as to elicit an intracellular response, including a partial agonist. The term "partial agonist" shall be taken to mean an agonist that elicits a weaker intracellular response than oxytocin. An agonist may comprise an antibody, peptide or small molecule. In one example, an agonist of an oxytocin receptor comprises a derivative or analog of oxytocin e.g., one or more of: 9-deamidooxytocin, carbetocin, 4-threonine, 7-glycine-oxytocin (TG-OT), 2-D-tyrosine-oxytocin, 5-D-asparagine-oxytocin or 1-hemi-D-cysteine-oxytocin. For example, carbetocin elicits long-lasting activity compared to native oxytocin. One or more other analogs of oxytocin described herein may also function as oxytocin analogs. A peptidyl receptor agonist may be linear or cyclic.

In one example, an agonist of an oxytocin receptor comprises WAY-267,464, a high-affinity, potent and selective non-peptide agonist of the oxytocin receptor, with negligible affinity for the vasopressin receptor. WAY-267,464 has been shown to cross the blood-brain-barrier to a significantly greater extent than exogenously applied oxytocin, and in animal tests produces centrally-mediated oxytocinergic actions such as anxiolytic effects, albeit with no apparent anti-depressant effect. These attributes suggest utility of WAY-267,464 or a pharmaceutically acceptable salt, hydrate or solvate thereof, or an enantiomeric form of WAY-267,464, or a racemic mixture of stereoisomers, in the treatment or prevention of problem drinking, especially in anxious subjects such as those withdrawing from alcohol or who drink at harmful or hazardous levels to combat anxiety.

In another example, an oxytocin receptor agonist comprises one or more benzyl carbamates or ureas, e.g., selected from the group consisting of: 4-methyl-1-(N-(2-methyl-4-(2, 3,4,5-tetrahydro-1,5-benzodiazepin-4-on-1-ylcarbonyl)-b enzylcarb amoyl)-L thioprolyl)perhydro-1,4-diazepine, 4-methyl-1-(N-(2-methyl-4-(1-methyl-4,10-dihydropyrazolo[5,4-b][1,5]benzodiazepin-5-yl-carbonyl)benzylcarbamoyl)-L-thioprolyl) perhydro-1,4-diazepine, 4,4-dimethyl-1-(N-(2-methyl-4-(1-methyl-4,10-dihydropyrazolo[5,4-b][1,5]benzodiazepin-5-ylcarbonyl)benzylcarbamoyl)-L-thioprolyl) perhydro-1,4-diazepinium iodide, 4-methyl-1-(N-(2-methyl-4-(5,6,7,8-tetrahydrothieno[3,2-b]azepin-4-ylcarbonyl)benzyl-carbamoyl)-L-thioprolyl) perhydro-1,4-diazepine, 4-methyl-1-(N-(2-methyl-4-(5,6,7,8-tetrahydrothieno[3,2-b]azepin-4-ylcarbonyl)benzyloxycarbonyl)-L-prolyl)perhydro-1,4-diazepine, (4R)—N"-(2-chloro-4-(5,6,7,8-tetrahydrothieno[3,2-b]azepin-4-ylcarbonyl)benzyl-carbamoyl)-4-methoxy-L-proline-N-methyl-N-(2-picolyl)amide, 1-((4R)—N'-(2-chloro-4-(5,6,7,8-tetrahydrothieno[3,2-b]azepin-4-ylcarbonyl)benzyl-carbamoyl)-4-methoxy-L-prolyl)-4-(1-pyrrolidinyl) piperidine, and mixtures thereof. These compounds can be prepared by standard chemical manipulations as described e.g., in WO/2003/000692.

In another example, a derivative or analog of oxytocin, or an agonist of an oxytocin receptor is an antagonist or inverse agonist of a vasopressin receptor or has no affinity for a vasopressin receptor e.g., it is other than vasopressin i.e., (3-phenylalanine, 8-arginine) oxytocin or other than vasotocin i.e., (8-arginine) oxytocin or other than oxypressin i.e., (3-phenylalanine) oxytocin.

As used herein, the term "antagonist" shall be taken to mean an agent that binds e.g., competitively or non-competitively to a vasopressin receptor however does not activate an intracellular response initiated by the active form of a vasopressin receptor, and can thereby inhibit the intracellular response mediated by the receptor, and/or inhibit an agonist or partial agonist of a vasopressin receptor. An antagonist typically does not diminish a baseline intracellular response in the absence of an agonist or partial agonist of a vasopressin receptor. In contrast, an "inverse agonist" of a vasopressin receptor is an agent that binds to either the endogenous form of a vasopressin receptor or to a constitutively-activated form of a vasopressin receptor and inhibits a baseline intracellular response initiated by the active form of the receptor below the normal baseline activity detected in the absence of an agonist or partial agonist of the receptor.

In another example of the present invention, a pharmaceutically-acceptable salt, solvate or hydrate of oxytocin, oxytocin derivative, oxytocin analog or oxytocin receptor agonist according to any example hereof is employed. For example, an acetate salt may be employed e.g., oxytocin acetate hydrate. In another example, the salt is a chloride salt. Exemplary solvates comprise the active compound in a pharmaceutically acceptable or other suitable solvent e.g., water, an alcohol such as ethanol or butanol, or buffered solution. Solubility enhancing agents e.g., one or more detergents may also be employed.

In another example of the present invention, a racemic mixture comprising different stereoisomers e.g., enantiomers, of an oxytocin analog or oxytocin receptor agonist according to any example hereof is employed.

In another example of the present invention, a stereoisomer e.g., enantiomer, of an oxytocin analog or oxytocin receptor agonist according to any example hereof is employed.

The oxytocin peptide or a derivative or analog thereof, or a peptidyl agonist of an oxytocin receptor can be a natural product or produced by synthetic or recombinant means. Processes for the production of oxytocin are described e.g., in U.S. Pat. Nos. 2,938,891 or 3,076,797. Oxytocin and several analogs thereof including carbetocin are commercially-available. For example, a peptide described herein can be prepared by chemical synthesis using either automated or manual solid phase synthetic technologies known in the art.

Oxytocin is also approved by the U.S. Food and Drug Administration for intravenous use to induce labor in pregnant women as well as for the treatment of postpartum hemorrhage.

Screening to Identify Oxytocin Derivatives and Analogs and Oxytocin Receptor Agonists Novel oxytocin derivatives and analogs, and novel oxytocin receptor agonists may be identified and/or isolated by screening natural compounds, antibodies, small molecules, peptides and proteins for one or more functionalities of oxytocin such as a functionality described herein. For example, such compounds are assayed in primary screens for an ability to form an association neurophysin 1 in vitro, in situ or in vivo, and/or an ability to bind to an oxytocin receptor in vitro or in situ or in vivo, and/or an ability to elicit signal transduction from an oxytocin receptor in vitro, in situ or in vivo, and/or an ability to stimulate production of oxytocin in vivo. Secondary screening is then performed to determine suitability in treatment and/or prevention of problem drinking e.g., in animal-based trials and/or human trials such as according to any procedure exemplified herein.

Previously-isolated products may be screened directly i.e., without additional purification or isolation.

For isolation of oxytocin derivatives and analogs or oxytocin receptor agonists, the compounds are derived from a complex source e.g., an animal, plant, microorganism such as a bacterium, fungus, or a combination of such sources, or an extract of an organism, organ, tissue or cell derived from such sources. Alternatively, oxytocin derivatives and analogs or oxytocin receptor agonists may be isolated from one or more synthetic or recombinant sources e.g., one or more peptide libraries e.g., cyclic peptide libraries, and/or one or more antibody libraries, and/or one or more small molecule libraries.

For example, a small molecule analog or oxytocin receptor agonist may be identified from a library of small molecules according to any example as described herein. Techniques for synthesizing small organic compounds will vary considerably depending upon the compound, however such methods is well known to those skilled in the art. In one example, informatics is used to select suitable chemical building blocks from known compounds, for producing a combinatorial library and/or selecting a library that is suitable as a source material. For example, QSAR (Quantitative Structure Activity Relationship) modeling approach uses linear regressions or regression trees of compound structures to determine suitability e.g., based on structures of known derivatives, analogs and receptor agonists. The software of the Chemical Computing Group, Inc. (Montreal, Canada) uses high-throughput screening experimental data on active as well as inactive compounds, to create a probabilistic QSAR model, which is subsequently used to select lead compounds. The Binary QSAR method is based upon three characteristic properties of compounds that form a "descriptor" of the likelihood that a particular compound will or will not perform a required function: partial charge, molar refractivity (bonding interactions), and logP (lipophilicity of molecule). Each atom has a surface area in the molecule and it has these three properties associated with it. All atoms of a compound having a partial charge in a certain range are determined and the surface areas (Van der Walls Surface Area descriptor) are summed. The binary QSAR models are then used to make activity models or ADMET models, which are used to build a combinatorial library. Accordingly, lead compounds identified in initial screens, can be used to expand the list of compounds for screening applications.

In another example, an antibody-based analog or receptor agonist may be identified from an antibody library. Antibodies useful in the present invention are produced and screened according to conventional procedures known in the art e.g., U.S. Pat. No. 5,541,101. As used herein, the term "antibody" refers to intact monoclonal or polyclonal antibodies, immunoglobulin (IgA, IgD, IgG, IgM, IgE) fractions, humanized antibodies, or recombinant single chain antibodies, as well as fragments thereof, such as, for example Fab, $F(ab)_2$, and Fv fragments. In the present context, an antibody having the requisite functionality of an oxytocin analog or oxytocin receptor agonist may be selected from a source material comprising an anti-idiotypic antibody prepared against an antibody that binds to oxytocin or a functional derivative or analog of oxytocin, and/or comprising an antibody prepared against the oxytocin receptor or a fragment thereof forming part of the interaction site between oxytocin and the receptor. Antibodies are prepared against by any of a variety of techniques known to those of ordinary skill in the art, and described, for example in, Harlow and Lane (In: Antibodies: A Laboratory Manual, Cold Spring Harbor Laboratory, 1988). In one such technique, an immunogen comprising the antigenic polypeptide is initially injected into any one of a wide variety of animals (e.g., mice, rats, rabbits, sheep, humans, dogs, pigs, chickens and goats). Peptide or protein-derived immunogens may be produced conveniently by recombinant expression means, or artificially generated, such as by chemical synthesis (e.g., BOC chemistry or FMOC chemistry). Antibodies may be prepared to small molecules, peptides, and polypeptide fragments of low immunogenicity by prior-conjugation with a hapten e.g., bovine serum albumin, keyhole limpet hemocyanin, or polylysine, and then immunizing with the conjugate. The immunogen, optionally conjugated to a hapten, is injected into an animal host according to a predetermined schedule, generally incorporating one or more booster immunizations, and blood is collected from the animal(s). Optionally, the immunogen is injected in the presence of an adjuvant e.g., Freund's complete or incomplete adjuvant, lysolecithin, or dinitrophenol, to enhance the immune response to the immunogen. Monoclonal or polyclonal antibodies specific for the polypeptide are then purified from blood isolated from an animal by, for example, affinity chromatography using the polypeptide coupled to a suitable solid support. Monoclonal antibodies specific for the antigenic polypeptide of interest are prepared, for example, using the technique of Kohler and Milstein, *Eur. J. Immunol.* 6:511-519 (1976) and improvements thereto. Alternatively, a monoclonal antibody is produced using a human B-cell hybridoma technique e.g., Kozbar et al., *Immunol. Today* 4:72, (1983), or EBV-hybridoma technique e.g., Cole et al. *Monoclonal Antibodies in Cancer Therapy*, (1985) Allen R. Bliss, Inc., pages 77-96. Methods for screening combinatorial antibody libraries are also described e.g., Huse et al., *Science* 246:1275 (1989).

In another example, a peptidyl derivative, analog or receptor agonist may be identified from one or more peptide libraries e.g., one or more libraries of random peptides or aptamers, and/or one or more libraries of conformationally-constrained peptides e.g., wherein the peptides are cyclized, and/or one or more libraries of peptides capable of forming secondary structures or super-secondary structures with or without cyclization. For example, the production peptide by inclusion of a thioredoxin loop or phylomers. Such peptides will generally be oxytocin peptidomimetics i.e., the screened peptides are not known to have a functionality of oxytocin prior to screening and are demonstrated by screening to mimic a functionality of oxytocin. For example, means for producing peptidomimetics capable of forming secondary structures or super-secondary structures with or without cyclization are described e.g., U.S. Pat. No. 7,270,969 to Phylogica Limited. Techniques for cyclization of peptides are well-known in peptide chemistry e.g., amide bond formation via juncture of N-terminal amine and C-terminal carboxylic acid groups to form head-to-tail cyclic peptides, amide bond formation via juncture of a γ-amino or δ-amino or ε-amino group and a C-terminal carboxylic acid group to form a head-to-tail cyclic peptide or a lactam or peptide loop comprising only a part of the peptide, disulfide bridge formation via incorporation of cysteines and subsequent oxidation, by aryl-aryl linkage via oxidative coupling of aromatic residues such as tyrosine or by Stille or Negishi or Suzuki cross-coupling reactions between O-tyrosine intermediates, or an aryl-ether linkage via juncture of aromatic groups using an ether linkage or oxidative C—O phenolic coupling of halogenated derivatives of tyrosine and tyramine. The production of head-to-tail cyclic peptides, lactams, cyclodipeptides, cyclic tripeptides, cyclic tetrapeptides, and cyclic pentapeptides is described e.g., Spatola et al. In: Combinatorial peptide and nonpeptide libraries: a handbook, (ed. Jung, G), VCH Verlagsgesellschaft mbH, Germany (1996), Chapter 11, and Feliu et al. *Int. J. Peptide Res. Ther.* 11, 53-97 (2005).

Any one or more of the foregoing complex sources of compounds may be screened by a functional assay to isolate there from an oxytocin derivative, oxytocin analog or oxytocin receptor agonist. This may require repeated screening of so-called "test compounds" to eventually purify the compound free or substantially free of contaminants. It is to be understood that the following assays can be utilized in separately or collectively and in any order determined empirically to identify or isolate the desired product at a level of purity and having an activity ascribed to it suitable for use in the methods of the invention. The activity and purity of the compounds determined by these assays make the compound suitable of formulations e.g., oral, injectable and/or inhalable medicaments for treatment and/or prophylaxis.

Assays for functional oxytocin derivatives, analogs and oxytocin receptor agonists are described herein, and may be readily derived from disclosures of such assays in the art e.g., Hasbi et al., *Mol. Endocrin.* 18, 1277-1286 (2004), U.S. Pat. Nos. 5,541,101, or 5,466,584.

In one exemplary functional assay, binding of a test compound to cells expressing a human oxytocin receptor is performed. For example, HEIS-293 cells or COS-7 cells or Chinese Hamster Ovary (CHO) cells or melanocytes stably transfected with the human oxytocin receptor e.g., U.S. Pat. No. 5,466,584 to Rohto Pharmaceutical Co. Ltd., Osaka, Japan, may be produced and employed. Briefly, cells transfected with a human oxytocin receptor are cultured by performing cycles of growth to confluence, collection, washing, trypsinization, and seeding into fresh medium. Adherent cells are collected, washed, separated e.g., using an enzyme-free dissociation medium, and collected by centrifugation. The collected cells are then homogenized, the homogenate is clarified by centrifugation, and the soluble fraction ultracentrifuged e.g., at 100,000 ×g to pellet cell membranes. Cell membranes are suspended in a suitable buffer e.g., 50 mM Tris/HCl, pH 7.4 containing 0.1% (w/v) BSA and 0.1 mM PMSF. For radioligand binding assay of derivatives, analogs, or oxytocin receptor agonists, different concentrations of one or more test compounds are combined with membrane suspensions and [$^3$H]oxytocin. Control reactions may comprise unlabeled oxytocin or unlabeled carbetocin (positive control), or buffer or DMSO (negative control). Following incubation for a time and under conditions sufficient for binding of oxytocin to the oxytocin receptor to occur, reactions are stopped e.g., by filtration of reactions on filter paper e.g., using a cell harvester such as Tomtek and Printed filtermat-B filter paper. Filter paper is dried, impregnated with scintillant e.g., MeltiLex B/H melt-on scintillation wax sheeting, and the radioactivity determined using a betaplate scintillation counter. High throughput reactions are performed using a 96-well format microtiter plate. Functionality of the oxytocin derivative, analog or oxytocin analog is determined by reduced binding of [$^3$H]oxytocin compared to the negative control.

Alternatively, or in addition, agonist-induced phosphorylation of the oxytocin receptor is determined. For example, cells e.g., CHO cells or COS-7 cells or HEK-293 cells transfected with hemagglutinin (HA)-tagged oxytocin receptor are incubated with [$^{32}$P] and then treated with unlabelled test compound or unlabelled oxytocin. The HA-tagged receptors are immune-precipitated from cell homogenates or other cell extract using an anti-HA antibody, immune complexes are resolved e.g., by SDS-PAGE, and the incorporation of labeled phosphate into the receptor is determined. Cells may be transfected with vector alone, and incubated with or without test compound as a negative control. Cells expressing the hemagglutinin-tagged receptor may be incubated with oxytocin or carbetocin or other known functional oxytocin derivative or analog or oxytocin receptor agonist, as a positive control. Phosphate incorporation in to the receptor may be expressed as agonist-induced increase in [$^{32}$P]-labeled receptor. Test compounds producing enhanced [$^{32}$P]-labeled receptor relative to a negative control are functional.

Alternatively, or in addition, agonist-induced interactions of a G protein-coupled receptor kinase (GRK) with the oxytocin receptor may be assayed in the presence and absence of a test compound e.g., in real time such as by time-resolved bioluminescence resonance energy transfer (BRET). Physical association between the GRK and oxytocin receptor may also be demonstrated by co-immune-precipitation of endogenous GRK with agonist-activated receptor. For example, in cells e.g., HEK-293 cells or CHO cells or COS-7 cells, transfected with both a fusion protein comprising oxytocin receptor and luciferase e.g., *Renilla* luciferase (RL), and a fusion protein comprising β-arrestin and a yellow fluorescent protein (YFP), addition of oxytocin or a functional derivative or analog of oxytocin or an agonist of the oxytocin receptor produces enhanced energy transfer between the luciferase donor and the YFP acceptor, as determined by an increase in the BRET ratio, indicative of an agonist-induced association between the oxytocin receptor and β-arrestin. Because agonist-induced internalization of the oxytocin receptor is mediated by arrestin, an agonist-induced association between the oxytocin receptor and β-arrestin in intact cells is indicative of activation of signaling through the receptor.

Alternatively, or in addition, one or more test compounds may be assayed for functionality in an animal-based system wherein the ability of the test compound to elicit a known functionality of oxytocin is determined. For example, animal-based systems permit in vivo determination of an ability of a test compound to stimulate uterine smooth muscle contraction during labor, and/or to trigger a milk ejection reflex in mammary myoepithelial cells during lactation, and/or produce an anxiolytic effect e.g., in an Open-Field model of anxiety e.g., Uvnas-Moberg et al., *Pharmacol. Biochem. Behav.* 49, 101-106 (1994) or "punished crossing test" such as that conducted in a four-plate apparatus e.g., Aron et al. *Neuropharmacol.* 10: 459-469 (1971), and/or to reverse a deficit in prepulse inhibition of the acoustic startle reflex (PPI) following administration of a psychotomimetic drug e.g. MK801 or amphetamine e.g., Rahman et al., U.S. Pat. Publication No. 20070117794. For such animal-based tests, murine animals e.g., rats and mice, are particularly suited, including wild-type animals and oxytocin knock-out animals e.g., Young et al., *Adv. Exp. Med. Biol.* 449, 231-240 (1998). An advantage of using oxytocin knock-out animals is a lower background activity of receptor activation, and reduced competition for receptor activation by endogenous oxytocin. Such oxytocin-deficient animals do not permit evaluation of the effect(s) of test compounds on feed-forward mechanisms that may otherwise enhance endogenous oxytocin production.

Test compounds that have been identified or isolated using one or more primary screens are validated by subsequent screening for an ability to reduce problem drinking in one or more animal models of problem drinking behavior. Such methods are exemplified herein. For example, an ability of a test compound to reduce self-administration of alcohol may be determined by administering the compound to an alcohol-preferring murine animal e.g., the Sardinian alcohol-preferring rat or P rat model or an animal that has developed an alcohol preference following exposure to alcohol in utero. The animal may be alcohol naïve or an animal that has been fed previously with ethanol or other alcohol on a regular basis. Administration may be performed conveniently by injection or oral ingestion in such animal models. Sardinian alcohol non-preferring rats may be employed as negative controls in such experiments. A placebo may also be administered as a negative control. Oxytocin or carbetocin or other known functional analog or derivative or known oxytocin receptor agonist may be employed as a positive control. Reviews of the P rat are provided by Crabbe et al., *Science* 264: 1715-1723 (1994) and Li et al., *Alcohol and Alcoholism* 29: 697-700 (1994). See also Brodie et al., *Alcohol & Alcoholism* 32: 19-22 (1997). Test compounds that reduce self-administration of alcohol and/or promote abstinence, or alternatively, reduce the adoption of an alcohol preference in alcohol naïve animals, are identified or isolated from such screens.

An in silico or in vitro analytical method and/or industrial process may be employed to carry a test compound isolated or identified in a screening method according to any example hereof into pilot scale production or industrial scale production.

This invention also encompasses know how pertaining to oxytocin derivatives and analogs and oxytocin receptor agonists prepared or isolated by the method described according to any example hereof. Accordingly, the present invention also provides a process for identifying or isolating an oxytocin derivative or analog or oxytocin receptor agonist, said process comprising:

(i) performing a method as described herein according to any example to thereby identify a compound having functionality as an oxytocin derivative or analog or oxytocin receptor agonist;
(ii) optionally, determining the amount of the compound;
(iii) optionally, determining the structure of the compound; and
(iv) providing the compound or the name or structure of the compound such as, for example, in a paper form, machine-readable form, or computer-readable form.

As used herein, the term "providing the compound" shall be taken to include any chemical or recombinant synthetic means for producing said compound (with or without derivitization) or alternatively, the provision of a compound that has been previously synthesized by any person or means.

In one example, the compound or the name or structure of the compound is provided with an indication as to its use e.g., as determined by a screen described herein.

The present invention additionally provides a process for producing a compound having functionality as an oxytocin derivative or analog or oxytocin receptor agonist or for identifying or isolating said compound, said process comprising:
(i) performing a method as according to any example hereof to thereby identify or isolate a compound having functionality as an oxytocin derivative or analog or oxytocin receptor agonist;
(ii) optionally, determining the amount of the compound;
(iii) optionally, determining the structure of the compound;
(iv) optionally, providing the name or structure of the compound such as, for example, in a paper form, machine-readable form, or computer-readable form; and
(v) providing the compound.

In one example, the compound or the name or structure of the compound is provided with an indication as to its use e.g., as determined by a screen described herein.

The present invention also provides a process of manufacturing having functionality as an oxytocin derivative or analog or oxytocin receptor agonist for use in the treatment or prevention of problem drinking in a subject, said process comprising:
(i) performing a method according to any example hereof to thereby identify or isolate a compound having functionality as an oxytocin derivative or analog or oxytocin receptor agonist; and
(ii) using the compound in the manufacture of a therapeutic for treatment or prevention of problem drinking in a subject.

In one example, a process or method according to any example hereof further comprises isolating a test compound.

Formulations

Oxytocin, or other compound having functionality as an oxytocin derivative or analog or oxytocin receptor agonist, or a pharmaceutically-acceptable salt, solvate, hydrate thereof, including any isolated stereoisomer or racemic mixture, is formulated for use with at least one pharmaceutically acceptable carrier or excipient or diluent e.g., suitable for inhalation or oral administration or injection.

Excipients will typically be included in the dosage form e.g., to improve solubility and/or bioadhesion. Suitable excipients include solvents, co-solvents, emulsifiers, plasticizers, surfactants, thickeners, pH modifiers, emollients, antioxidants, and chelating agents, wetting agents, and water absorbing agents. Formulations may also include one or more additives, for example, dyes, colored pigments, pearlescent agents, deodorizers, and odor maskers.

Diluents or fillers increase the bulk of a solid dosage form so that a practical size is provided for compression of tablets or formation of beads and granules. Suitable diluents include, but are not limited to dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Formulations may also comprise one or more dispersants e.g., phosphate-buffered saline (PBS), saline, glucose, sodium lauryl sulfate (SLS), polyvinylpyrrolidone (PVP), polyethylene glycol (PEG), and hydroxypropylmethylcellulose (HPMC).

Formulations may also comprise one or more binders to impart cohesive qualities to a solid dosage formulation, and thus ensure that a tablet, bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose ("HPMC"), microcrystalline cellulose ("MCC"), hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone (PVP).

Formulations may also comprise one or more lubricants to facilitate manufacture or ingestion of a solid dosage unit e.g., a tablet. Examples of suitable lubricants include, but are not limited to, magnesium stearate, calcium stearate, stearic acid, glycerol behenate, polyethylene glycol, talc, and mineral oil.

Formulations may also comprise one or more disintegrants to facilitate dosage form disintegration after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP.

Formulations may also comprise one or more stabilizers and/or preservatives (e.g., E216, E218, and chlorobutanol hemihydrate) to inhibit or retard drug decomposition reactions e.g., by oxidation or bacterial action.

Formulations may also comprise one or more surfactants. Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-00 monolaurate, polyoxyethylene monolaurate, polysorbates, polyoxyethylene octylphenylether, PEG-1000 cetyl ether, polyoxyethylene tridecyl ether, polypropylene glycol butyl ether, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

If desired, solid formulations e.g., tablets, beads, granules, or particles may also contain an amount of a non-toxic auxiliary substance such as a wetting or emulsifying agent, dye, or pH buffering agent.

Pharmaceutical formulations may be presented in unit dose forms containing a predetermined amount of active agent i.e., oxytocin, or a derivative or analog thereof, or an oxytocin receptor agonist, per unit dose. The concentration of active agent may vary depending upon whether or not the formulation is for prevention or therapy, the route of administration, half-life of the compound following administration by the selected route, and the age, weight and condition of the patient including e.g., the severity of problem drinking being treated. For example a unit dose may comprise about 1 μg to 10 ug, or 0.01 mg to 1000 mg, or 0.1 mg to 250 mg, of oxytocin, or a derivative or analog thereof, or an oxytocin receptor agonist, or a pharmaceutically-acceptable salt, solvate, hydrate thereof, including any isolated stereoisomer or racemic mixture. In another example, oxytocin, or a derivative or analog thereof, or an oxytocin receptor agonist, or a pharmaceutically-acceptable salt, solvate, hydrate thereof, including any isolated stereoisomer or racemic mixture may be formulated such that the concentration of active agent is at least about 1% (w/w) or at least about 5% (w/w) or at least about 10% (w/w) or at least about 25% (w/w) based on the total weight of the pharmaceutical composition.

To prepare pharmaceutical formulations, one or more of oxytocin, an oxytocin derivative, an oxytocin analog, or oxytocin receptor agonist is/are mixed with a pharmaceutically acceptable carrier or excipient for example, by mixing with physiologically acceptable carriers, excipients, or stabilizers in the form of, e.g., lyophilized powders, slurries, aqueous solutions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Formulation of a pharmaceutical compound will vary according to the route of administration selected (e.g., solution, emulsion, capsule). For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils, for instance. Intravenous vehicles can include various additives, preservatives, or fluid, nutrient or electrolyte replenishers and the like (See, generally, Remington's Pharmaceutical Sciences, 17th Edition, Mack Publishing Co., Pa., 1985). For inhalation, the agent can be solubilized and loaded into a suitable dispenser for administration (e.g., an atomizer, nebulizer or pressurized aerosol dispenser).

Pharmaceutical formulations can be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations can be prepared by any method known in the art of pharmacy, for example by bringing into association the active ingredient with the carrier(s), diluent(s) or excipient(s).

In one example, pharmaceutical formulations are adapted for oral administration e.g., as capsules, soft gels, or tablets; powders or granules, solutions or suspensions in aqueous or non-aqueous liquids, edible foams or whips, or oil-in-water liquid emulsions or water-in-oil liquid emulsions. An oral formulation may comprise an intragranular phase comprising an effective amount of a agonist or compound of the present invention and at least one carbohydrate alcohol and an aqueous binder. The pharmaceutical formulation may be substantially lactose-free. Preferred carbohydrate alcohols for such formulations are selected from the group consisting of mannitol, maltitol, sorbitol, lactitol, erythritol and xylitol. Preferably, the carbohydrate alcohol is present at a concentration of about 15% to about 90%. A preferred aqueous binder is selected from the group consisting of hydroxypropyl cellulose, hydroxypropyl methylcellulose, carboxymethyl cellulose sodium, polyvinyl pyrrolidones, starches, gelatins and the like. A binder is generally present in the range of from about 1% to about 15% by weight. The intragranular phase can also comprise one or more diluents, such as, for example, a diluent selected from the group consisting of microcrystalline cellulose, powdered cellulose, calcium phosphate-dibasic, calcium sulfate, dextrates, dextrins, alginates and dextrose excipients. Such diluents are also present in the range of about 15% to about 90% by weight. The intragranular phase can also comprise one or more disintegrants, such as, for example, a disintegrant selected from the group consisting of a low substituted hydroxypropyl cellulose, carboxymethyl cellulose, calcium carboxymethylcellulose, sodium carboxymethyl cellulose, sodium starch glycollate, crospovidone, croscarmellose sodium, starch, crystalline cellulose, hydroxypropyl starch, and partially pregelatinized starch. A disintegrant is generally present in the range of from about 5% to about 20% by weight. Such a formulation can also comprise one or more lubricants such as, for example, a lubricant selected from the group consisting of talc, magnesium stearate, stearic acid, hydrogenated vegetable oils, glyceryl behenate, polyethylene glycols and derivatives thereof, sodium lauryl sulphate and sodium stearyl fumarate. A lubricant is generally present in the range of from about 0.5% to about 5% by weight. Such formulations are made into a tablet, capsule, or soft gel e.g., by a process comprising mixing a agonist or compound of the invention and at least one carbohydrate alcohol to form a dry blend, wet granulating the dry blend with an aqueous binder so as to obtain an intragranular phase, and further formulating the resulting intragranular phase so as to provide the formulation. Typically, tablet or capsules is prepared to contain an appropriate unit dosage e.g., from 0.001 mg to 1000 mg.

Alternatively, a liquid or semi-solid pharmaceutical formulation for oral administration e.g., a hard gel or soft gel capsule comprising one or more of oxytocin, an oxytocin derivative, an oxytocin analog, or oxytocin receptor agonist, may be prepared comprising:
(a) a first carrier component comprising from about 10% to about 99.99% by weight of one or more of oxytocin, an oxytocin derivative, an oxytocin analog, or oxytocin receptor agonist;
(b) an optional second carrier component comprising, when present, up to about 70% by weight of one or more of oxytocin, an oxytocin derivative, an oxytocin analog, or oxytocin receptor agonist;
(c) an optional emulsifying/solubilizing component comprising, when present, from about 0.01% to about 30% by weight of one or more of oxytocin, an oxytocin derivative, an oxytocin analog, or oxytocin receptor agonist;
(d) an optional anti-crystallization/solubilizing component comprising, when present, from about 0.01% to about 30% by weight of one or more of oxytocin, an oxytocin derivative, an oxytocin analog, or oxytocin receptor agonist; and
(e) an active pharmacological agent comprising from about 0.01% to about 80% of one or more of oxytocin, an oxytocin derivative, an oxytocin analog, or oxytocin receptor agonist in an anhydrous crystal form.

The first carrier component and optional second carrier component generally comprise, independently, one or more of lauroyl macrogel glycerides, caprylocaproyl macrogel glycerides, stearoyl macrogel glycerides, linoleoyl macrogel glycerides, oleoyl macrogel glycerides, polyalkylene glycol, polyethylene glycol, polypropylene glycol, polyoxyethylene-polyoxypropylene copolymer, fatty alcohol, polyoxyethylene fatty alcohol ether, fatty acid, polyethoxylated fatty acid ester, propylene glycol fatty acid ester, fatty ester, glycerides of fatty acid, polyoxyethylene-glycerol fatty ester, polyoxypropylene-glycerol fatty ester, polyglycolized glycerides, polyglycerol fatty acid ester, sorbitan ester, polyethoxylated sorbitan ester, polyethoxylated cholesterol, polyethoxylated castor oil, polyethoxylated sterol, lecithin, glycerol, sorbic acid, sorbitol, or polyethoxylated vegetable oil.

The emulsifying/solubilizing component generally comprises one or more of metallic alkyl sulfate, quaternary ammonium compounds, salts of fatty acids, sulfosuccinates, taurates, amino acids, lauroyl macrogol glycerides, caprylocaproyl macrogolglycerides, stearoyl macrogol glycerides, linoleoyl macrogol glycerides, oleoyl macrogol glycerides, polyalkylene glycol, polyethylene glycol, polypropylene glycol, polyoxyethylene-polyoxypropylene copolymer, polyoxyethylene fatty alcohol ether, fatty acid, polyethoxylated fatty acid ester, propylene glycol fatty acid ester, polyoxyethylene-glycerol fatty ester, polyglycolized glycerides, polyglycerol fatty acid ester, sorbitan ester, polyethoxylated sorbitan ester, polyethoxylated cholesterol, polyethoxylated castor oil, polyethoxylated sterol, lecithin, or polyethoxylated vegetable oil.

The anti-crystallization/solubilizing component, when present, generally comprises one or more of metallic alkyl sulfate, polyvinylpyrrolidone, lauroyl macrogol glycerides, caprylocaproyl macrogolglycerides, stearoyl macrogol glycerides, linoleoyl macrogol glycerides, oleoyl macrogol glycerides, polyalkylene glycol, polyethylene glycol, polypropylene glycol, polyoxyethylene-polyoxypropylene copolymer, fatty alcohol, polyoxyethylene fatty alcohol ether, fatty acid, polyethoxylated fatty acid ester, propylene glycol fatty acid ester, fatty ester, glycerides of fatty acid, polyoxyethylene-glycerol fatty ester, polyglycolized glycerides, polyglycerol fatty acid ester, sorbitan ester, polyethoxylated sorbitan ester, polyethoxylated cholesterol, polyethoxylated castor oil, polyethoxylated sterol, lecithin, or polyethoxylated vegetable oil.

By appropriate formulation of oxytocin for oral administration, an oxytocin derivative, an oxytocin analog, or oxytocin receptor agonist, the effective concentration in a body fluid such as plasma or cerebrospinal fluid can be enhanced, relative to a concentration in adipose tissue. For example, oxytocin, an oxytocin derivative, an oxytocin analog, or oxytocin receptor agonist may be formulated with a hydrophobic polymer, preferably a bioadhesive polymer and optionally encapsulated in or dispersed throughout a microparticle or nanoparticle. The bioadhesive polymer improves gastrointestinal retention via adherence of the formulation to the walls of the gastrointestinal tract. Suitable bioadhesive polymers include polylactic acid, polystyrene, poly(bis carboxy phenoxy propane-co-sebacic anhydride) (20:80) (poly (CCP: SA)), alginate (freshly prepared); and poly(fumaric anhydride-co-sebacic anhydride (20:80) (poly(FA:SA)), types A (containing sudan red dye) and B (undyed). Other high-adhesion polymers include p(FA:SA) (50:50) and non-water-soluble polyacrylates and polyacrylamides. Preferred bioadhesive polymers are typically hydrophobic enough to be non-water-soluble, but contain a sufficient amount of exposed surface carboxyl groups to promote adhesion e.g., non-water-soluble polyacrylates and polymethacrylates; polymers of hydroxy acids, such as polylactide and polyglycolide; polyanhydrides; polyorthoesters; blends comprising these polymers; and copolymers comprising the monomers of these polymers. Preferred biopolymers are bioerodable, with preferred molecular weights ranging from 1000 to 15,000 kDa, and most preferably 2000 to 5000 Da. Polyanhydrides e.g., polyadipic anhydride ("p(AA)"), polyfumaric anhydride, polysebacic anhydride, polymaleic anhydride, polymalic anhydride, polyphthalic anhydride, polyisophthalic anhydride, polyaspartic anhydride, polyterephthalic anhydride, polyisophthalic anhydride, poly carboxyphenoxypropane anhydride and copolymers with other polyanhydrides at different mole ratios, are particularly preferred. Blends of hydrophilic polymers and bioadhesive hydrophobic polymers can also be employed. Suitable hydrophilic polymers include e.g., hydroxypropylmethylcellulose, hydroxypropylcellulose, carboxymethylcellulose, polyvinylalcohols, polyvinylpyrrollidones, and polyethylene glycols. Other mucoadhesive polymers include DOPA-maleic anhydride co polymer, isopthalic anhydride polymer, DOPA-methacrylate polymers, DOPA-cellulosic based polymers, and DOPA-acrylic acid polymers.

Alternatively, the oxytocin, or a derivative or analog thereof, or an oxytocin receptor agonist may be encapsulated or molecularly dispersed for oral administration in a polymer to reduce particle size and increase dissolution. The polymers may include polyesters such as poly(lactic acid) or P(LA), polycaprylactone, polylactide-coglycolide or P(LGA), poly hydroxybutyrate poly β-malic acid); polyanhydrides such as poly(adipic)anhydride or P(AA), poly(fumaric-co-sebacic) anhydride or P(FA:SA), poly(sebacic)anhydride or P(SA); cellulosic polymers such as ethylcellulose, cellulose acetate, cellulose acetate phthalate, etc; acrylate and methacrylate polymers such as Eudragit RS 100, RL 100, E100 PO, L100-55, L100, S100 (distributed by Rohm America) or other polymers commonly used for encapsulation for pharmaceutical purposes and known to those skilled in the art. Also suitable are hydrophobic polymers such as polyimides. Blending or copolymerization sufficient to provide a certain amount of hydrophilic character can be useful to improve wetability of the materials. For example, about 5% to about 20% of monomers may be hydrophilic monomers. Hydrophilic polymers such as hydroxylpropylcellulose (HPC), hydroxpropylmethylcellulose (HPMC), carboxymethylcellulose (CMC) are commonly used for this purpose.

Oral formulations may be an "immediate release" formulations e.g., that release at least 85% (wt/wt) of the oxytocin, or a derivative or analog thereof, or an oxytocin receptor agonist, within 60 minutes in vitro. Alternatively, the formulation may be a "controlled release" formulation that releases drug more slowly than an immediate release formulation i.e., it takes longer than 60 minutes to release at least 85% (wt/wt) of the drug in vitro. To extend the time period for release, the ratio of active agent to polymer can be increased. Increased relative drug concentration is believed to have the effect of increasing the effective compound domain size within the polymer matrix thereby slowing dissolution. In the case of a polymer matrix containing certain types of hydrophobic polymers, the polymer will act as a mucoadhesive material and increase the retention time of the active compound in the gastrointestinal tract. Increased drug dissolution rates combined with the mucoadhesive properties of the polymer matrix increase uptake of the active compound and reduce differences found in the fed and fasted states for the compounds.

In another example, a formulation comprising one or more of oxytocin, an oxytocin derivative, an oxytocin analog, or oxytocin receptor agonist is adapted for administration by inhalation. In accordance with this example, the active agent is formulated to produce a fine particle, dust or mist, which may be generated by means of a metered dose inhaler, nebulizer or insufflator. Spray compositions may be formulated as aerosols delivered from pressurized packs, such as a metered dose inhaler, with the use of a suitable liquified propellant. Capsules and cartridges comprising e.g., gelatine, may be produced for use in an inhaler or insufflator, wherein the oxytocin, oxytocin derivative, oxytocin analog, or oxytocin receptor agonist comprises a powder contained within the capsule or cartridge. The powder may be produced using a suitable powder base e.g., lactose or starch. Aerosol formulations are preferably arranged so that each metered dose or "puff" of aerosol contains about 0.001 µg to about 2000 µg of oxytocin, oxytocin derivative, oxytocin analog, or oxytocin receptor agonist.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close to the nose. Suitable formulations wherein the carrier is a liquid, for administration as a nasal spray or as nasal drops, include aqueous or oil solutions of the active ingredient.

The overall daily dose and the metered dose delivered by capsules and cartridges in an inhaler or insufflator will generally be double those with aerosol formulations.

In another example, a formulation comprising one or more of oxytocin, an oxytocin derivative, an oxytocin analog, or oxytocin receptor agonist is adapted for parenteral administration e.g., by subcutaneous or intravenous injection. Such formulations include aqueous and non-aqueous sterile injection solutions which may contain the antioxidants as well as buffers, bacteriostats and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets. In one example, oxytocin, an oxytocin derivative, an oxytocin analog, or oxytocin receptor agonist is formulated as an intravenous lipid emulsion or a surfactant micelle or polymeric micelle (see, e.g., Jones et al., *Eur. J. Pharmaceutics Biopharmaceutics* 48, 101-111, 1999; Torchilin *J. Clin, release* 73, 137-172, 2001 for parenteral administration.

Sustained release injectable formulations are produced e.g., by encapsulating oxytocin, an oxytocin derivative, an oxytocin analog, or oxytocin receptor agonist in porous microparticles comprising a pharmaceutical agent and a matrix material having a volume average diameter between about 1 µm and 150 µm, e.g., between about 5 µm and 25 µm diameter. In one example, the porous microparticles have an average porosity between about 5% and 90% by volume. In another example, the porous microparticles further comprise one or more surfactants, such as a phospholipid. The microparticles may be dispersed in a pharmaceutically acceptable aqueous or non-aqueous vehicle for injection. Suitable matrix materials for such formulations comprise a biocompatible synthetic polymer, a lipid, a hydrophobic molecule, or a combination thereof. For example, the synthetic polymer can comprise, for example, a polymer selected from the group consisting of poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate) (jointly referred to herein as "polyacrylic acids"), poly (butyric acid), poly(valeric acid), and poly(lactide-co-caprolactone), copolymers, derivatives and blends thereof. In a preferred example, the synthetic polymer comprises a poly (lactic acid), a poly(glycolic acid), a poly(lactic-co-glycolic acid), or a poly(lactide-co-glycolide).

Dosage and Administration

Selecting an administration regimen for a therapeutic or prophylactic composition depends on several factors, including whether or not the formulation is for prevention or therapy, the route of administration, half-life of the compound following administration by the selected route, and the age, weight and condition of the patient including e.g., the severity of problem drinking being treated. A good administration regimen optimizes the effective concentration of amount of oxytocin, an oxytocin derivative, an oxytocin analog, or oxytocin receptor agonist delivered to the site of action e.g., an oxytocin receptor with acceptable or minimum contraindications or side-effects. Formulations produced as described herein may be administered to a subject in need thereof by any acceptable route which effectively transports the oxytocin, an oxytocin derivative, an oxytocin analog, or oxytocin receptor agonist to an appropriate or desired site of action, e.g., oral, nasal, pulmonary, transdermal e.g., by passive or iontophoretic delivery, parenteral e.g. rectal, depot, subcutaneous, intravenous, intraurethral, intramuscular, or intranasal injection, or topical e.g., by application of an ophthalmic solution or an ointment.

A formulation is generally administered by dosing at predetermined intervals e.g., one dosage unit per day, one dosage unit per week, or daily dosage units for up to 7 days per week.

A suitable dosage unit comprises the oxytocin, an oxytocin derivative, an oxytocin analog, or oxytocin receptor agonist at a concentration of at least about 0.05 µg/kg body weight, or at least about 0.2 µg/kg, or at least about 0.5 µg/kg, or at least about 1 µg/kg, or at least about 10 µg/kg, or at least about 100 µg/kg, or at least about 0.2 mg/kg, or at least about 1.0 mg/kg, or at least about 2.0 mg/kg, or at least about 10 mg/kg, or at least about 25 mg/kg, or at least about 50 mg/kg e.g., Yang, et al. *New Engl. J. Med.* 349:427-434 (2003) or Herold et al. *New Engl. J. Med.* 346:1692-1698 (2002). The optimum dosage is subject to one or more factors e.g., the severity of the problem drinking behavior, the overall health of the patient, the method route and dose of administration, and the severity of side affects. Determination of the appropriate dose may be made by a clinician, e.g., using parameters or factors known or suspected in the art to affect treatment or predicted to affect treatment. Generally, the dose may commence with an amount somewhat less than the optimum dose and be increased by small increments thereafter until the desired or optimum effect is achieved relative to any negative side effects. Important diagnostic measures include those of symptoms of the disease and/or disorder being treated. Such parameters are described in general e.g., by Maynard, et al, In: A Handbook of SOPs for Good Clinical Practice, Interpharm Press, Boca Raton, Fla. (1996) or Dent In: Good Laboratory and Good Clinical Practice, Urch Publ., London, UK (2001).

An effective therapeutic dosage regimen can be expected to decrease alcohol intake by at least about 10% or 20% or 30% or 40% or 50%, or more, and in a proportion of patients, result in abstinence from alcohol. Such abstinence may be for up to 6 months or up to 12 months, or up to 2 years of for longer periods.

An effective prophylactic dosage regimen can be expected to delay or prevent alcohol intake in an alcohol naïve subject in the short to long term e.g., for up to several years.

The present invention is described further in the following non-limiting examples:

Example 1

Acute Effects of Oxytocin on Alcohol Consumption and Preference

This example demonstrates the efficacy of oxytocin therapy on alcohol consumption and preference, in an animal model of problem drinking.
Subjects
P rats (8 female and 8 male P rats) were provided by Professor Andrew Lawrence at the Howard Florey Institute, Melbourne, Australia. The animals were of adolescent age (i.e., 28 days-old) on arrival at the animal house. Animals were housed in same-sex cages at a density of 3-4 rats per cage. Over the following 2 months, animals received intermittent exposure to various alcoholic beverages in their home cages e.g., white wine, red wine, beer, Vodka Cruiser, Bacardi Breezer, but were alcohol-free for the month preceding testing.
General Procedure
Testing occurred in a lickometer apparatus. Rats were placed in a small metal cage where they have a choice of two tubes for supply of liquids, wherein the tube were designed such that every third lick at one tube delivered a small drop (0.07 ml) of 3% (w/v) sucrose solution, and every third lick at the other tube delivered a small amount of alcohol-containing beverage, in particular Vodka Cruiser (Raspberry Flavor), containing 5.0% (w/v) ethanol. Rats were exposed daily to 70 min sessions in the lickometer until their intake of sucrose and/or alcohol and preferences for these beverages had stabilized.
Test Procedure
One-half of the rats being tested were injected intra-peritoneally (I/P) with a single dosage of 0.3 mg/kg oxytocin, administered 10 min before their daily drinking session. The following day, these animals received a normal baseline test session with no further oxytocin dosing. The following day, one-half of the animals were administered I/P with 1 mg/kg oxytocin 10 min before the test session. Normal drinking sessions then continued for a further 4 days. During the same period, the other one-half of the rats were administered a placebo (vehicle) lacking oxytocin. Animals receiving the placebo were treated with oxytocin in exactly the same sequence as the treatment group, commencing one week after the start of testing. A final test to determine alcohol intake and alcohol preference was conducted after 55 days, to determine whether or not oxytocin induced lasting changes in drinking behavior.
Results.
Data in FIGS. 1 (*a*), (*b*) and (*c*) indicate that baseline preference for Vodka Cruiser approached 50% in P rats exposed to alcohol. Acute administration of oxytocin (0.3 and 1 mg/kg) produced a significant reduction in both Cruiser and Sucrose solution intake, consistent with an anorexic effect of the drug. Importantly, intake of the alcoholic beverage remained suppressed for at least 55 days following oxytocin, with a corresponding shift towards a preference for alcohol-free solution, and intake of alcohol-free solution.

Example 2

Oxytocin for Use in the Prevention of Problem Drinking

Figure 2:
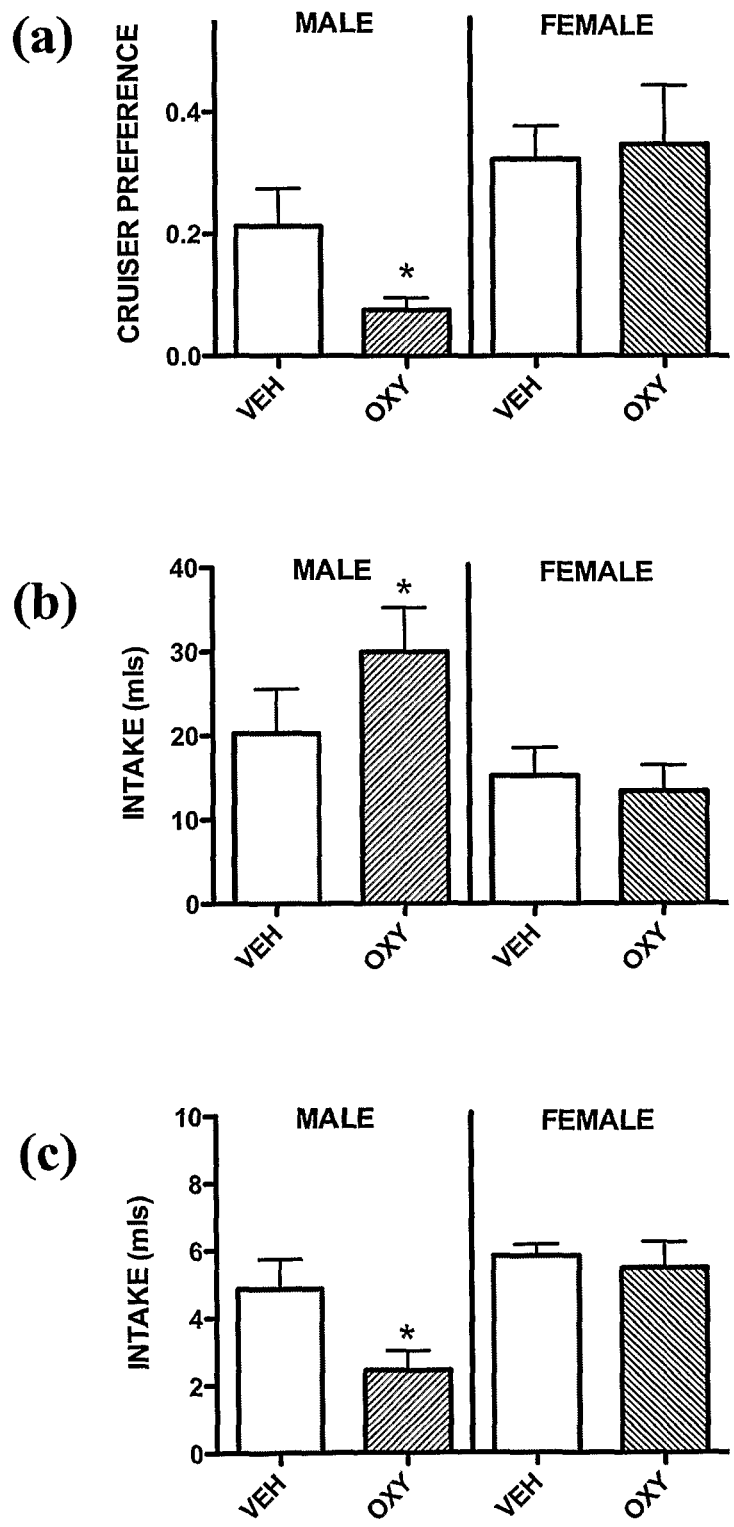
FIG. 2 provides a graphical representation showing the alcohol preferences and alcohol intakes by alcohol-naïve male P rats and female P rats that were treated with 10 dosage units of 1 mg/kg/day of a negative control vehicle (open bars) or oxytocin (filled bars). Alcohol preference (y-axis) was based on selection between a pre-mixed alcoholic beverage (Vodka Cruiser, 4.8% alcohol) and 3% sucrose solution one month after cessation of treatment. Panel (a) shows preference for Vodka Cruiser versus 3% sucrose solution in the final 4 days of testing in a lickometer. Male rats pre-treated with oxytocin showed significantly reduced preference for Cruiser over sucrose relative to the other test groups. Panel (b) shows intake of sucrose was higher in male oxytocin-treated rats relatively to both of the females groups. Panel (c) shows intake of Cruiser was lower in male oxytocin-treated rats than in any of the other 3 groups. Data are for n=3 male and n=4 female P rats per group. In summary, these data show that acquisition of a robust alcohol intake in males and females receiving negative control vehicle, however the preference for alcohol in both sexes was reduced significantly following treatment. The reduced acquisition of alcohol preference was greater in males compared to females. The data suggest that oxytocin is suitable for prevention of problem drinking FIG. 3 provides graphical representations showing anxiolytic effect of oxytocin in rats pre-treated with oxytocin (OXY) compared to empty vehicle (VEH), as determined by time to emergence from a small dark hide into a brightly-lit open field. Animals receiving oxytocin emerged more rapidly from their hide (panel a) and spent significantly less time hiding (panel b) than animals receiving the vehicle. n=24 per condition.

This example demonstrates the ability of oxytocin to prevent or delay alcohol intake by alcohol-naïve subjects in an animal model of problem drinking.
Subjects
P rats (8 female and 6 male P rats) of adult age (i.e., 150 days) were used in this study. Animals were maintained as described in example 1, however they received no alcohol prior to testing.
Drug Treatment
One-half of the rats (n=4 female and n=3 male) were given 10 injections of 1 mg/kg oxytocin (a single I/P injection per day for a total of 10 days). The other half of the rats received equivalent injections of placebo/vehicle lacking oxytocin. Two weeks later, the alcohol preferences of both sets of alcohol-naïve animals were tested. The same alcohol and alcohol-free solutions were employed as in example 1, and testing conditions were in the same lickometer apparatus. Testing in the lickometer (1×70 min session per day) continued for a total of 10 days during which time intake of sucrose and Vodka Cruiser were measured.
Results
Data in FIG. 2 show the proportion of total beverage intake consumed as Vodka Cruiser during the last 4 days of testing for both animal groups. Male animals, but not female animals, that had been pre-treated with oxytocin showed less intake of alcohol during the period tested.

Example 3

Treatment with Oxytocin Prevents Subsequent Alcohol Preference and Consumption

This example demonstrates that oxytocin is an effective preventive therapy against problem drinking in subjects who are not necessarily predisposed to problem drinking behavior, using an animal model comprising a common laboratory rat strain of Wistar rats, that show relatively high levels of alcohol intake but are not genetically selected for alcohol preference.

Subjects

Male Wistar rats (n=48) were obtained from the Animal Resource Centre (ARC), Perth, Western Australia, Australia. The animals were of early adolescent age (i.e., 21 days-old) on arrival and were young adults (i.e., 33 days-old) when oxytocin therapy commenced. The animals were housed and maintained as described in the preceding examples, except that animals were moved to individual housing during chronic exposure to alcohol.

Dosage Regimen

One-half of the rats (n=24) were administered 10 injections of 1 mg/kg oxytocin (1×I/P injection per day for a total of 10 days). The other half of the rats (n=24) received equivalent injections of placebo/vehicle lacking oxytocin.

Determination of Anxiety and Social Behavior

At 7 days following final injection of oxytocin, all rats were tested in an emergence test of anxiety. This 5 min test measures the willingness of rats to leave a small dark hide box and emerge into a brightly lit open field. Rats normally avoid brightly lit and open spaces. Three days later, the animals were tested in social interaction tests which measure the willingness of rats to engage in social behavior during a 10 min session in a darkened arena where they meet an unknown rat that has received the same drug treatment.

Alcohol Induction and Preference Testing in Treated Animals

A subset of the treated rats (n=8 per condition) were exposed to alcohol in the lickometer apparatus over a 10 day period. On the first day of testing, animals were exposed to a 70 min session in the lickometer during which a low-alcohol near-beer was provided at both lick tubes (Birell's Premium, containing 0.5% alcohol). On subsequent days, animals were exposed to further 70 min test sessions during which near-beer supplemented with increasing amounts of absolute ethanol were provided at both lick tubes i.e., to produce a beer comprising 1.5%, 2.5%, 3.5% and finally 4.5% ethanol. The concentration of ethanol was then maintained at 4.5% for all subsequent testing.

After 9 days of lickometer testing, the rats were given free access to 4.5% ethanol containing beer for a 24-day period in their home cages. Standard rat chow and tap water were also available in the home cages. Alcohol intakes and body weights were measured daily.

Results

1. Emergence Test

Figure 3:
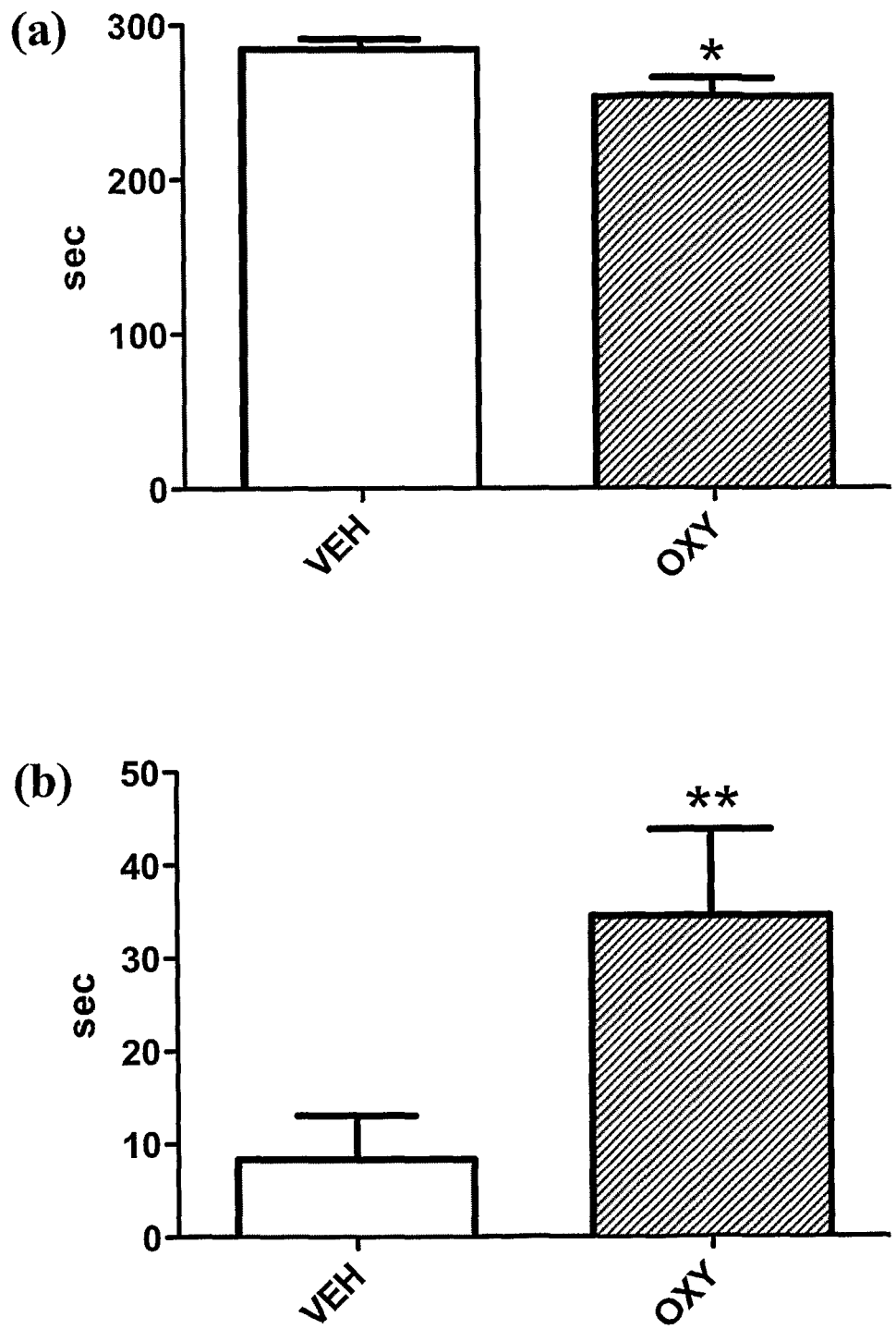

Data shown in FIG. 3 confirm the anxiolytic activity of oxytocin in test animals. Rats that had received a course of oxytocin treatment that ended 7 days before the emergence test was conducted showed reduced anxiety relative to control rats, as determined by a greater likelihood of emergence into the open field, and reduced time hiding.

2. Social Interaction Test

Figure 4:
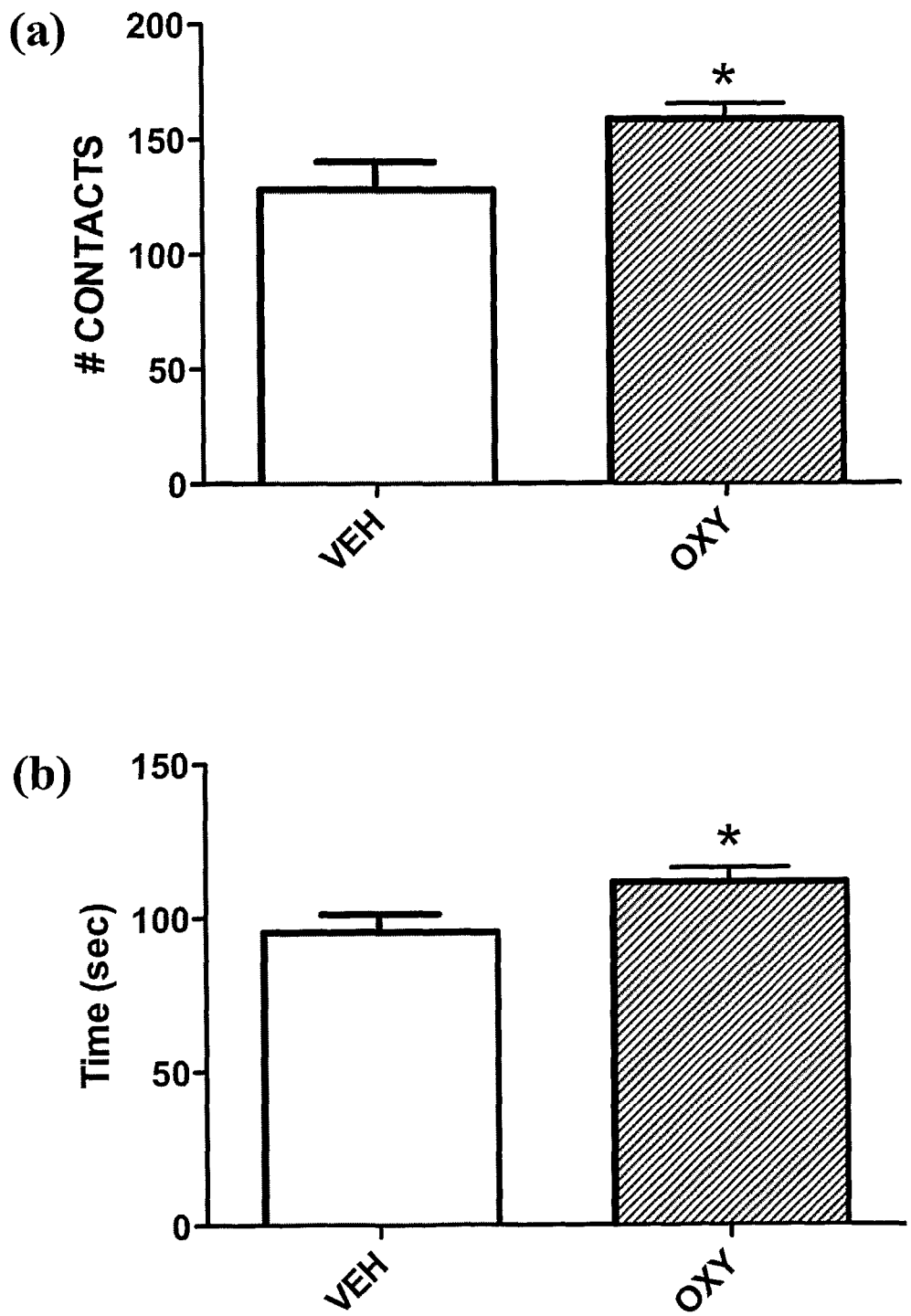
FIG. 4 provides graphical representations showing prosocial effects of oxytocin in rats pre-treated with oxytocin (OXY) compared to empty vehicle (VEH), as determined by number of social contacts in a 10 minute social interaction test (panel a) and time spent within one and half body lengths of another rat (proximal time, panel b). Data indicate significantly higher numbers of social contacts and proximal times for animals receiving oxytocin compared to vehicle.

Data shown in FIG. 4 confirm the anxiolytic activity of oxytocin by demonstrating that oxytocin therapy enhanced socialization in the test animals, as determined by increased numbers of social contacts and increased time spent in close proximity to an unknown animal. In summary, oxytocin therapy increased levels of social interaction, and decreased social anxiety in the test animals.

3. Induction of Alcohol Intake

Figure 5:
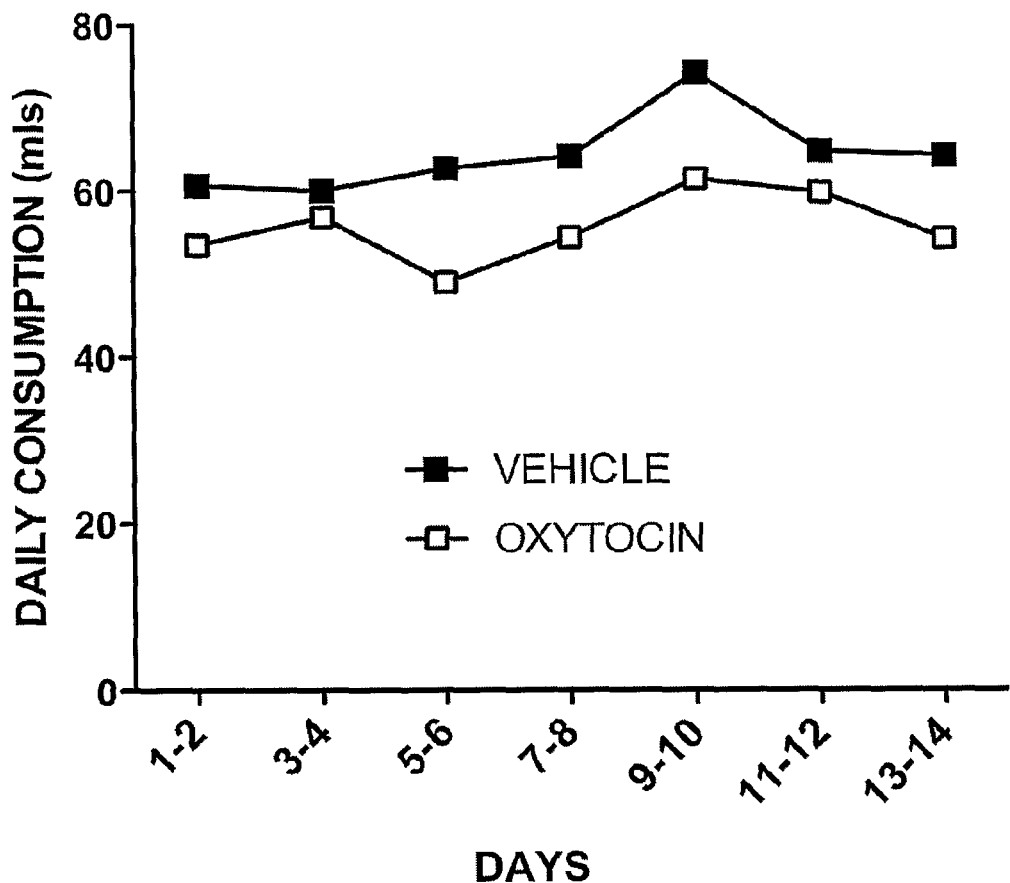
FIG. 5 provides a graphical representation showing average daily intake of full strength beer by singly-housed male Wistar rats receiving a placebo vehicle (Filled boxes; n=8) or oxytocin (open boxes, n=8) one month before commencement (day 0). Data are presented as average intake for each two days of testing. Data indicate significantly reduced alcohol consumption by animals receiving a preventive dosage unit of oxytocin.
Figure 6:
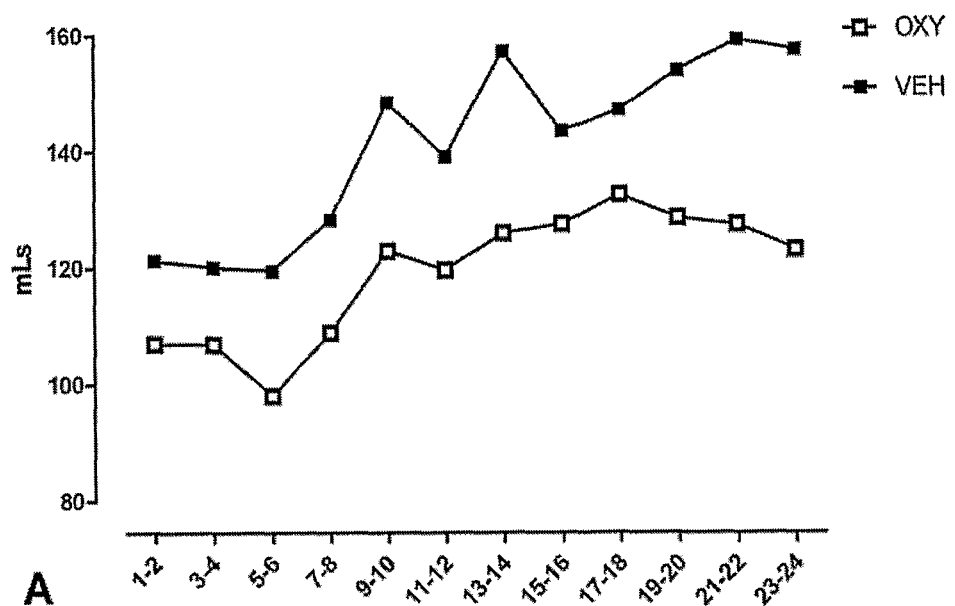
FIG. 6 provides graphical representations showing average daily intake of full strength beer (panel A) and water (panel B) by singly-housed alcohol naïve Wistar rats that had previously been administered a daily intraperitoneal (IP) injection of a placebo vehicle (Filled boxes; n=8) or oxytocin (open boxes, n=8) for ten days, ending three weeks (day 0) before 24 days exposure to continuous supply of the alcohol or water. Data are presented as average intake for each two days of testing. Data indicate that pre-treatment of animals with oxytocin significantly reduced an escalation of alcohol consumption and/or prevented increased alcohol consumption or problem drinking in subjects receiving oxytocin as a prophylactic, compared to animals receiving saline vehicle. Oxytocin prophylaxis did not significantly modify consumption of water during the same period, indicating that the prophylactic benefit of oxytocin in preventing problem drinking such as by reducing an increment in alcohol consumption, is selective on alcohol consumption.
Figure 6:
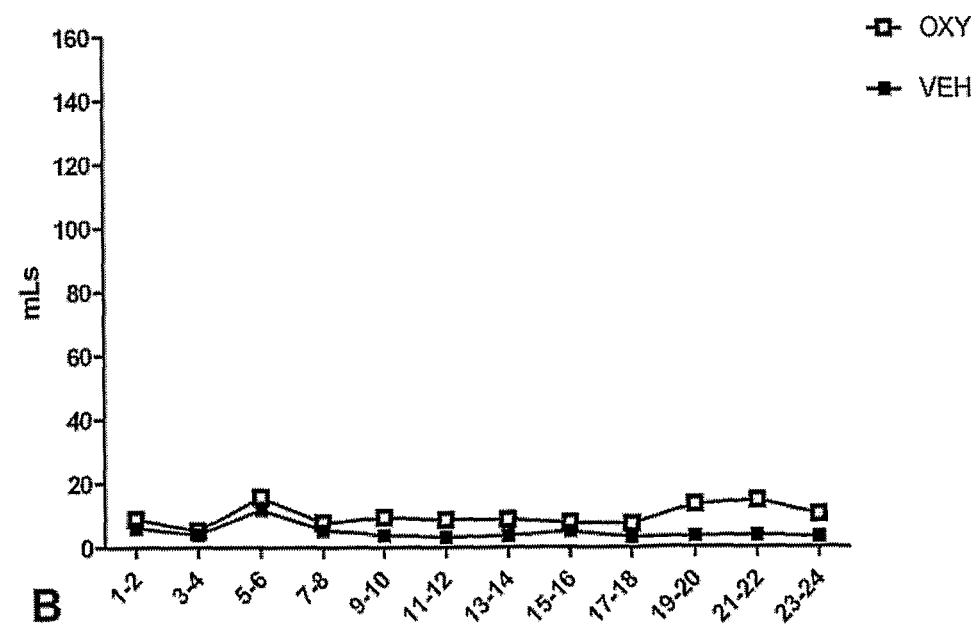
Figure 7:
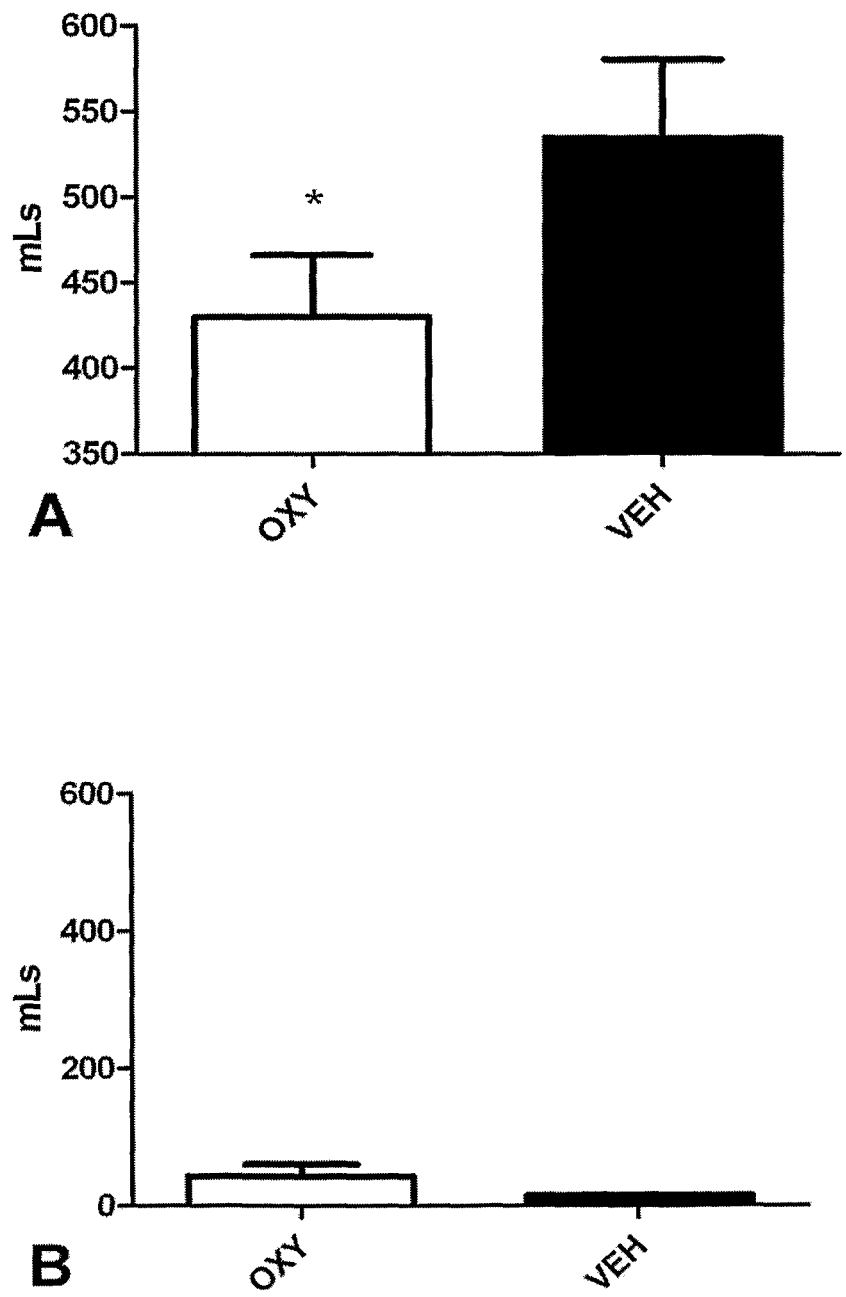
FIG. 7 provides graphical representations showing total consumption (ml) full strength beer (panel A) and water (panel B) by animals in the final week of the experiment described in the legend to FIG. 6. Data indicate that prophylactic treatment with oxytocin (OXY), but not saline vehicle (VEH), significantly reduced later consumption of alcohol, even several weeks after administration of the prophylactic had ceased. The asterisk indicates a threshold level of alcohol consumption in animals that had received the oxytocin (OXY) prophylaxis that is significantly different to that for animals that had received saline vehicle (VEH). In contrast, there was no significant difference in total water consumption over this period (panel B). These data further emphasize the selective long-term preventive benefit of prophylaxis comprising administration of oxytocin to subjects that do not have an established pattern of heavy drinking or problem drinking.

Data shown in FIGS. 5-7 indicate that rats administered with one or more preventive dosages of oxytocin and then provided free access to full strength beer in their home cages consumed consistently less alcohol than animals that been provided with a placebo during the same period and maintained under the same conditions.

In the experiment described in the legend to FIG. 5, animals that did not receive any oxytocin before being exposed to a continuous alcohol supply then consumed about 60-75 ml of beer per day (FIG. 5), which equates to about 5-6 g/kg of pure ethanol per day. In contrast, animals that had received oxytocin prophylaxis i.e., wherein the final injection of oxytocin had been administered about 30 days before exposure to alcohol showed consistently less alcohol intake. The oxytocin pre-treated rats appeared healthy and had the same body weight and food intake as controls.

In the experiment described in the legend to FIG. 6, animals that did not receive any oxytocin before being exposed to a continuous alcohol supply then consumed incrementally higher levels of alcohol, commencing at about 120 ml of beer per day or about 10 g/kg of pure ethanol per day, increasing gradually over 24 days to about 160 ml beer per day or about 13.3 g/kg of pure ethanol per day (FIG. 6, panel A, filled boxes). Thus, in the absence of oxytocin prophylaxis, animals developed a problem drinking pattern characterized by incremental alcohol consumption. In contrast, animals that had received a daily oxytocin prophylaxis over a 10-day period, wherein the final injection of oxytocin had been administered about 21 days before exposure to alcohol showed consistently less alcohol intake. In animals that received oxytocin prophylaxis, initial alcohol consumption was reduced by about 10% to only about 110 ml of beer per day or about 9 g/kg of pure ethanol per day, increasing marginally to only about 120 ml beer per day or 130 ml beer per day or about 10-10.8 g/kg of pure ethanol per day (FIG. 6, panel A, open boxes). Water intake in both groups of animals was unchanged in the same period, indicating that the effect of oxytocin prophylaxis on reducing an increment in alcohol consumption is selective.

Data in FIG. 7 also indicate that the prophylactic benefit of oxytocin in preventing problem drinking e.g., by preventing or reducing a preference for alcohol and/or by preventing incremental alcohol consumption, extends beyond the short-term. Data presented in FIG. 7 indicate clearly that, even after several weeks following the cessation of oxytocin prophylaxis, alcohol consumption in pre-treated subjects is reduced significantly compared to animals receiving a saline placebo. For example, alcohol consumption is reduced by about 10% or 20% or 30% or 40% in the medium term to long term following cessation of prophylaxis.

The testing performed in these examples is a particularly stringent test of the effect of oxytocin in reducing problem drinking, because drug treatment was several weeks before testing was carried out, and animals were subjected to a stressor of being housed individually, and no significant alternative rewards were provided to the animals.

Example 4

Figure 8:
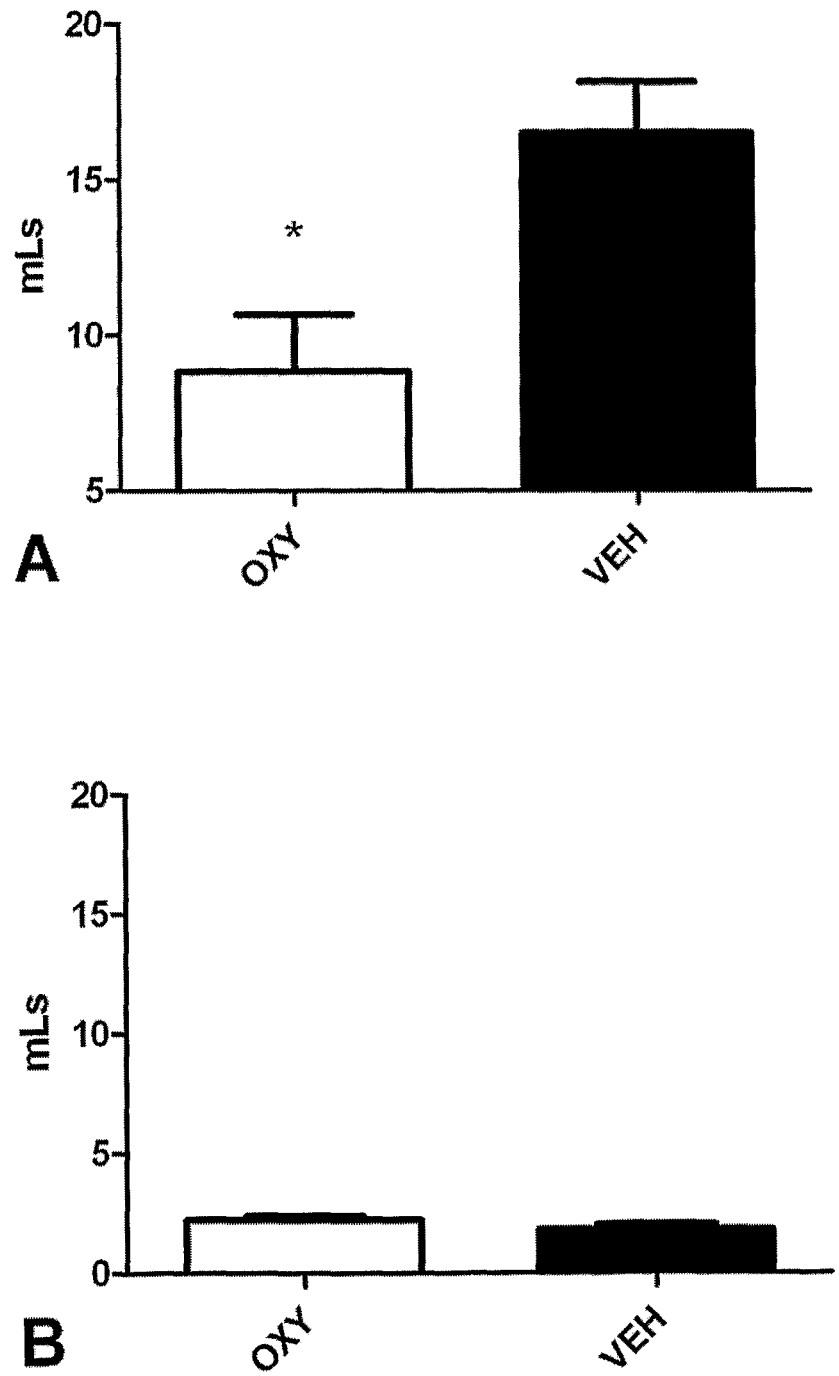
FIG. 8 provides graphical representations showing total consumption (ml) of full strength beer (panel A) and water (panel B) in rats having established patterns of pathologically-high alcohol consumption over several months, in a 2.5 hr period following intraperitoneal (IP) injection with 1 mg/kg oxytocin (OXY, n=8) or saline vehicle (VEH, n=8). The asterisk indicates a threshold level of alcohol consumption that is significantly different to that for animals receiving saline vehicle placebo. Data indicate that treatment with oxytocin, but not saline vehicle, significantly reduced beer consumption (panel A) in animals that had established problem drinking over several months. Alcohol consumption in animals treated with oxytocin was reduced in the short-term by about 25% to about 40% or about 50% or about 60%. In contrast, consumption of water was unchanged in animals receiving oxytocin or saline vehicle placebo. These data demonstrate that oxytocin selectively-reduces alcohol consumption in alcohol dependent subjects.

Prophylactic Efficacy of Oxytocin in Reducing Alcohol Consumption in the Short-Term in Subjects Having Established Patterns of Problem Drinking Alcohol-dependent animals were provided a single injection i/p of oxytocin (1 mg/kg body weight) and their alcohol consumption levels in the 2.5 hr period following therapy were determined. As shown in FIG. 8, alcohol consumption in subjects having established patterns of problem drinking, or alcohol dependence, is reduced significantly following therapy with oxytocin. In contrast, water consumption was not affected, indicating that oxytocin is selective in reducing alcohol consumption relative to water.

Example 5

Efficacy of an Acute Booster Dosage Unit of Oxytocin in Decreasing Alcohol Consumption In this example, animals that have been treated previously with oxytocin, and exhibiting demonstrable reduction in alcohol preference and intake resulting from that treatment, are provided with a booster injection of oxytocin e.g., at the end of 24 days of chronic alcohol consumption following a protocol described in the preceding example hereof. Alcohol consumption is determined to establish efficacy of oxytocin therapy in prolonging the reduction in alcohol consumption achieved with primary therapy e.g., by virtue of an additive or synergistic effect on the earlier dosing regimen.

Example 6

Efficacy of an Acute Dosage Unit of Oxytocin in Decreasing Reinstated Alcohol Consumption Following Abstinence In this example, animals that have been treated previously with oxytocin, and exhibiting demonstrable abstinence from alcohol resulting from that treatment, are provided with a stressor and/or exposed to acute dosage of alcohol and/or exposed to chronic dosages of alcohol with or without one or more booster injections of following protocols described in the preceding examples hereof. Such reinstatement protocols are accepted animal models of relapse processes in problem drinkers e.g., in human alcoholism e.g., McGregor et al., *Alcohol & Alcoholism* 40, 35 (2005). Alcohol consumption and optionally, anxiety and/or social interaction are determined to establish efficacy of oxytocin in preventing relapse and providing anxiolytic benefit and enhanced socialization during relapse in problem drinkers.

Example 7

Efficacy of Oxytocin Analogs and Derivatives and Oxytocin Receptor Analogs

The protocols of examples 1 through 6 are followed employing one or more oxytocin derivatives, oxytocin analogs and oxytocin receptor analogs, including e.g., 4-threonine-1-hydroxy-deaminooxytocin and/or 4-serine, 8-isoleucine-oxytocin and/or 9-deamidooxytocin and/or 7-D-proline-oxytocin and/or (2,4-diisoleucine)-oxytocin and/or carbetocin and/or 4-threonine, 7-glycine-oxytocin (TG-OT) and/or oxypressin and/or deamino-6-carba-oxytoxin(dC60) and/or deamino-di-carba-oxytoxin. As negative controls, the effect(s) of one or more oxytocin receptor antagonists e.g., [1-(3-mercaptopropanoic acid)-2-(O-ethyl-D-tyrosine)-4-threonine-8-ornithine]oxytocin and/or 1-($\beta$-mercapto-$\beta$,$\beta$,-cyclopentamethylenepropionic acid, 2-O-methyltyrosine, 4-threonine, 8-ornithine, 9-tyrosylamide] vasotocin and/or [1-(S)Pmp,2-DTrp,6-Pen,8-Arg]oxytocin (OTA), administered in place of oxytocin or a derivative or analog thereof or an oxytocin receptor agonist is/are also determined. The antagonist [1-(3-mercaptopropanoic acid)-2-(O-ethyl-D-tyrosine)-4-threonine-8-ornithine]oxytocin is also known as atosiban. The antagonist 1-($\beta$-mercapto-$\beta$,$\beta$-cyclopentamethylenepropionic acid, 2-O-methyltyrosine, 4-threonine, 8-ornithine, 9-tyrosylamide]vasotocin is also known as [1-D($CH_2$)$_5$,Tyr(ME)$_2$,Thr4,Tyr-$NH_2$(9)]ornithine vasotocin. The antagonist [1-(S)Pmp,2-DTrp,6-Pen,8-Arg]oxytocin (OTA) is a modified oxytocin comprising $\beta$,$\beta$-(3-thiapentamethylene)-$\beta$-mercaptopropionic acid at position 1, D-Trp at position 2, penicillamine at position 6 and arginine at position 8 of oxytocin. Alcohol consumption and alcohol-seeking behavior and optionally, anxiety and/or social interaction are determined to establish efficacy of such molecules.

Example 8

Alcohol Consumption in Untreated and Oxytocin-Treated Oxytocin Knock-Out Mice In this example, oxytocin knock-out animals are subjected to the protocol(s) described in preceding example(s) hereof and alcohol consumption and preference, and optionally, anxiety and socialization are determined. Mice lacking expression of a gene encoding oxytocin have been described e.g., Pedersen et al., *Genes, Brain Behavior* 5, 274 (2006). Mice having a higher baseline predisposition to alcohol than corresponding e.g., otherwise iosogenic, wild-type mice are treated with oxytocin to establish efficacy of oxytocin in reducing alcohol consumption, promoting and/or extending a period of abstinence, preventing relapse and providing anxiolytic benefit and enhanced socialization during relapse.

Example 9

Neural Mechanisms Underlying the Effect(s) of Oxytocin Therapy

In this example, the neural pathways affected by oxytocin therapy in problem drinkers are assessed in animal models described in the preceding examples. Levels of oxytocin and oxytocin receptor and receptor occupation rates are determined hourly or every 4-6 hours or 12-hourly in the first 1-7 days following commencement of therapy, and daily thereafter. For example, the effect of oxytocin therapy in problem drinkers on levels of oxytocin and oxytocin receptors are determined by recording oxytocin and oxytocin receptor levels and oxytocin receptor occupation over time in one or more of central nervous system e.g., basal ganglia, thalamus, hypothalamus including ventromedial hypothalamus and ventromedial hypothalamic nucleus, supraoptic nucleus, paraventricular nucleus, lateral septal nucleus, basal nuclei of Meynert, basolateral amygdaloid nucleus, stria terminalis (BSNT), central amygdaloid nucleus, ventral subiculum olfactory bulb, olfactory nucleus and/or reproductive system including myometrium and endometrium, and/or blood, establishes half life information on therapeutics, blood-brain barrier penetrability, receptor occupation, and regulation of oxytocin expression following administration e.g., feed-forward mechanism. These analyses will provide information on hypothalamus oxytocin and oxytocin receptor gene expression and may point to the mechanisms underlying the acute and long-term effects of oxytocin on alcohol intake.

Example 10

Human Pre-Clinical and Clinical Studies

In this example, the efficacy of oxytocin therapy as described in animal models e.g., one or more of Examples 1 through 6 is demonstrated in a sample of the human population.

1. Study 1

In a first clinical study in humans, the effects of intranasal oxytocin therapy on stress and alcohol-related cues are determined in a population of alcohol-dependent adults and in a population of non-dependent problem drinkers, e.g., problem drinkers that score higher than 8 on the Alcohol Use Disorders Identification Test (AUDIT), however do not meet diagnostic criteria for alcohol dependence. The underlying mechanisms of intranasal oxytocin during exposure to stress and alcohol related cues in adult alcohol-dependent and adult non-dependent problem drinkers are determined.

In particular, at least twenty male and female adults reporting alcohol dependence according to the Diagnostic and Statistical Manual of Mental Disorders, Fourth Edition (DSM-IV) as determined by the Structured Clinical Interview for the DSM-IV (SCID-IV) are recruited from the community to participate in a laboratory based investigation on the role of oxytocin in stress-related alcohol craving. All alcohol-dependent participants have a current diagnosis of alcohol dependence according to the SCID-IV, score higher than 8 on the Alcohol Use Disorders Identification Test (AUDIT), and score at least 10 on the Impaired Control Questionnaire (ICQ).

An additional twenty male and female non-dependent adults are recruited that score higher than 8 on the Alcohol Use Disorders Identification Test (AUDIT).

Exclusion criteria from participation in all studies are as follows:
1. Subjects with a diagnosis of severe medical illness;
2. subjects with current suicidal or homicidal ideation;
3. female subjects who are currently or recently pregnant or lactating or breast feeding;
4. subjects with reported allergy to E216, E218, or chlorobutanol hemihydrate as preservatives;
5. subjects with nasal obstruction, discharge, or bleeding;
6. subjects with a diagnosed cardiovascular problem e.g., heart disease, history of heart attack;
7. subjects who habitually drink large volumes of water; and
8. subjects who currently undergo any smoking or alcohol cessation pharmacological/behavioral treatment e.g., varenicline, naltrexone, psychotherapy and are not willing to cease this treatment prior to participation in the study.

To confirm subject suitability for trial, recent substance use is confirmed by urine toxicology, a pregnancy test is performed on all females under 50 years of age, menstrual cycle and contraceptive usage is determined for female subjects, and heart functions are assessed by electrocardiogram (ECG).

Participants are interviewed firstly by telephone to determine their suitability based on inclusion and exclusion criteria supra. Participants who are deemed suitable, and provide their consent to participate, attend the BMRI for a clinical and medical interview comprising assessment by SCID-IV, AUDIT, Problem Drinking Questionnaire (PDQ), 90-day Time Line Follow Back (TLFB), urine toxicology, pregnancy testing, and ECG.

Participants considered suitable for participation following clinical and medical evaluation are assessed further to determine base-line parameters according to the Depression Anxiety Stress Scale-21 (DASS-21), Positive and Negativity Affect Scale (PANAS), and Alcohol Urge Questionnaire (AUQ).

Neuropsychological testing is also performed by conducting a battery of tests that take approximately 90 min to complete, assessing a broad range of cognitive domains. For example, pen-and-paper tasks are administered according to standardized instructions e.g., Lezak, *In: Neuropsychological Assessment* (3rd ed), New York, Oxford University Press (1995). In another example, computerized tests from the Cambridge Neuropsychological Test Automated Battery (CANTAB) are administered according to CANTAB manual protocols, on a PC fitted with a color touch-screen monitor. These tests are described e.g., by Owen et al., *Neuropsychologia* 33, 1-24 (1995) and Young et al., *Psychopharmacology*, 145, 260-266 (1999). Exemplary CANTAB tests include one or more of the following:
1. Learning and memory (visuospatial) testing of paired-associates learning, wherein subjects learn and then replicate the matching of complex stimuli to specific spatial locations on a computer screen within ten attempts, wherein the number of stimulus-location pairs increases from two to eight in each round.
2. Pattern recognition testing wherein subjects learn a series of twelve complex patterns and are then presented with pairs of patterns in two sets from which they are required to identify a familiar one.
3. Spatial recognition testing wherein subjects are required to learn the on-screen spatial position of five serially presented squares, with a subsequent forced-choice recognition between two locations, in four trials.
4. Simultaneous/delayed matching to sample testing wherein subjects must recognize a previously-presented stimulus item from among four very similar stimuli after a delay of e.g., 0, 4 or 12 seconds.
5. Spatial working memory testing, wherein subjects must locate counters hidden in boxes and avoid repetitious searching of locations.
6. A Tower of London test wherein central executive function is taxed by requiring subjects to rearrange a set of spheres to match a given target arrangement in a specified minimum number of moves, and accuracy and latency are recorded.

Subject also provide a saliva sample for cortisol analysis and are fitted with a heart rate (HR) and blood pressure (BP) monitor for regular monitoring of their heart rate and blood pressure at specific testing points throughout the study. Given that smoking behavior is closely associated with alcohol use, participants also provide information regarding smoking pattern according to the Fagerstrom Test for Nicotine Dependence (FTND). Participants also provide bloods for determination of baseline plasma oxytocin and cortisol levels.

Recruited subjects are administered placebo or oxytocin intranasally (80 IU per day: 40 IU at 9:00 am and 40 IU at 9:00 pm) over a period of 7 days, following completion of baseline measurements. Subjects are instructed on self-administration procedures. Drug administration commences on the evening of the day of the clinical and medical interview and ceases on a morning one-week later, after 14 doses have been administered. Subjects are randomized to oxytocin-receiving or placebo-receiving groups, and the groups are stratified according to gender, age, and drinking behavior.

Subjects returning to the Brain and Mind Research Institute on the afternoon of the final day of testing are evaluated. Bloods and saliva are taken, and plasma oxytocin and cortisol levels and saliva cortisol are determined and compared to baseline levels before commencement of therapy. A urine toxicology test and alcohol breathalyzer test are also performed, to determine whether subjects have been alcohol-free and drug-free at the time of testing. Subjects are tested according to DASS-21, PANAS, 7-day TLFB, and AUQ, and neuropsychological evaluations e.g., according to CANTAB are performed. Changes in mood, drinking behavior and neuropsychology are evaluated for both groups by comparison with baseline evaluations. Changes in smoking behavior are evaluated by FTND testing and comparison with baseline evaluations. HR and BP records over the period and at cessation are also determined and compared to baseline levels before commencement of therapy.

Subjects also perform an impromptu speech task that is known to induce anxiety, to confirm the anxiolytic action of oxytocin therapy. In particular, subjects deliver a 5-minute speech on a widely-publicized topic familiar to most people e.g., climate change, which they have been misinformed previously is to be delivered by teleconference to a live audience. An eye tracker (Tobii Technology) in front of participants determines eye gaze during the speech task to assess the subject's tendencies to focus on negative cues presented from audience members. To assess changes in affect, alcohol craving, and physiology following the speech task, participants are subjected to a second round of PANAS, AUQ, and saliva cortisol testing, and their heart rates and blood pressures are determined.

Following the speech task, participants are presented with alcohol-related cues. In particular, subjects select their most-preferred alcoholic beverage from a variety of spirits, wines, and beer, pour a drink, raise it to their lips and smell it, but do not imbibe. To determine motivation of subjects to drink following presentation of the alcohol cues, participants press either one of two tally counters which they have been informed provides permission to either drink an alcoholic beverage of their choice when sufficient high number of counts are reached or to receive AUD 5.00 at the end of the experiment. Following exposure to the alcohol cues, participants are subjected to a third round of PANAS, AUQ, and saliva cortisol testing, and their heart rates and blood pressures are determined.

Data are analyzed using repeated measures MANOVA, to provide comparisons between self-reported levels of anxiety, stress and craving before and after treatment in the oxytocin-receiving group and placebo-receiving group, in addition to comparisons being made between physiological and biochemical indicia before and after treatment in the oxytocin-receiving group and placebo-receiving group.

For example, such testing indicates that subjects receiving oxytocin therapy have higher plasma oxytocin and lower plasma cortisol levels, and report lower subjective craving for alcohol, lower anxiety and stress, lower salivary cortisol, heart rate and arterial blood pressure during presentation of stress and alcohol cues compared to subjects receiving placebo.

1. Study 2

In a second clinical study in humans, the effect(s) of intranasal oxytocin therapy on alcohol self-administration are determined in a population of alcohol-dependent adults and in a population of non-dependent problem drinkers.

At least forty male and female adults are recruited from the community to the Brain and Mind Research Institute (BMRI) to participate in a laboratory based investigation looking at the impact of oxytocin on alcohol craving. Participants have a current diagnosis of alcohol dependence according to the Diagnostic and Statistical Manual of Mental Disorders, Fourth Edition (DSM-IV) as determined by the Structured Clinical Interview for the DSM-IV (SCID-IV) or are non-dependent subjects scoring higher than 8 on AUDIT. Male and female participants are chronic hazardous drinkers consuming more than 20 (females) or 25 (males) standard drinks per week (i.e., females: more than 200 g alcohol per week; males more than 250 g alcohol per week), respectively, and have not been abstinent more than 3 days per week in the 30 days preceding commencement of the trial as determined by AUDIT.

Exclusion criteria from participation are as described herein for Study 2, except that subjects are also excluded if presenting severe medical illness contraindicating alcohol use e.g., serum liver enzyme levels greater than or equal to 3-fold normal value.

All subjects are tested for baseline SCID-IV, AUDIT, PDQ, 90-day TLFB, DASS-21, PANAS, AUQ, FTND, urine toxicology, plasma oxytocin and cortisol, liver function testing, heart rate (HR), blood pressure (BP), and ECG, and females are pregnancy-tested and their menstrual cycles determined, as described herein above for Study 2. Neuropsychological evaluations are also performed e.g., according to CANTAB. Additionally, subjects are subjected to attention bias assessment task testing, wherein attention biases to alcohol-related cues are determined using e.g., stroop and dot-probe methodology. Subjects also participate in a reward learning computer task, to assess motivation for their alcohol consumption. Based on their test results, subjects are selected for recruitment in the study.

Recruited subjects are administered placebo or oxytocin intranasally (80 IU per day: 40 IU at 9:00 am and 40 IU at 9:00 pm) over a period of 7 days, following completion of baseline measurements. Subjects are instructed on self-administration procedures. Drug administration commences on the evening of the day of the clinical and medical interview and ceases on a morning one-week later, after 14 doses have been administered. Subjects are randomized to oxytocin-receiving or placebo-receiving groups, and the groups are stratified according to gender, age, and drinking behavior. Subjects are contacted by telephone daily to confirm medication compliance and determine adverse events.

Subjects returning to the BMRI on the afternoon of the final day of testing are evaluated. Bloods for plasma oxytocin and cortisol levels are collected before commencement. A urine toxicology test and alcohol breathalyzer test are also performed, to determine whether subjects have been alcohol-free and drug-free at the time of testing. Subjects are tested according to DASS-21, PANAS, 7-day TLFB, and AUQ, and neuropsychological evaluations e.g., according to CANTAB are performed. Changes in mood, drinking behavior and neuropsychology are evaluated for both groups by comparison with baseline evaluations. Changes in smoking behavior are evaluated by FTND testing and comparison with baseline evaluations. HR and BP records over the period and at cessation are also determined and compared to baseline levels before commencement of therapy.

Subjects are also provided an alcohol-priming drink (3 g/kg) being 1:3 (v/v) 80-proof liquor-of-choice: diluent e.g., an equicaloric, non-caffeinated, non-carbonated drink such as described by O'Malley et al., $Psychopharmacol.$ 160, 19 (2002), on completion of testing and allowed to consume it. At 50 min and 120 min following priming, subjects undergo two ad libitum drinking sessions, each of 1 hour duration in which time they consume up to four alcoholic drinks (15 g/kg), or alternatively, receive monetary reinforcement not to consume alcohol e.g., AUD 3.00 per drink not consumed as described by O'Malley et al., $Psychopharmacol.$ 160, 19 (2002). Participants remain under supervision until their breathalyzer reading falls below 0.05% alcohol. Blood Alcohol Concentration (BAC), blood pressure and heart rate are assessed 15 min before and every 10-30 min for a period of about 3 hours after priming e.g., at 10 min, 20 min, 30 min, 40 min, 80 min, 110 min, 150 min, and 180 min following the consumption of the priming drink. Subjective effects of alcohol e.g., mean of high, like, rush, feel-good, intoxicated, and mood, and potential adverse effects e.g., nausea, dizziness, jitters are assessed before priming and at 20 min, 40 min, 110 min, and 180 min following priming with alcohol see e.g., Schuckit et al., *Arch. Gen., Psychiatry* 41, 879 (1984), and Russell *J. Personality Soc. Psychol.* 39, 1161 (1980).

Data are analyzed using repeated measures MANOVA, to provide comparisons between alcohol consumed, mood, and physiological processes during drinking sessions of the oxytocin-receiving group and placebo-receiving group, in addition to comparisons being made between such indicia before and after treatment in the oxytocin-receiving group and placebo-receiving group.

For example, such testing indicates that subjects receiving oxytocin therapy have higher plasma oxytocin levels and lower plasma cortisol levels, and report lower subjective craving for alcohol, show lower levels of positive response to the alcohol primer, consume less alcohol, show a lower bias to alcohol-related cues, and show reduced reward motivation for alcohol consumption than subjects receiving placebo.

3. Study 3

In a third clinical study in humans, a double-blind, randomized and placebo-controlled study is conducted to determine the effect(s) of intranasal oxytocin therapy on alcohol self-administration in a population of alcohol-dependent adults and in a population of non-dependent problem drinkers. This study determines safety and efficacy of chronic intranasal oxytocin therapy for problem drinking.

At least 30 male and female alcohol-dependent adults and non-dependent problem drinkers are recruited according to the protocols described in the preceding examples hereof, to participate in a trial investigating chronic (4 week) intranasal oxytocin therapy for problem drinking e.g., alcohol-dependent subjects having a current diagnosis of alcohol dependence according to the Diagnostic and Statistical Manual of Mental Disorders, Fourth Edition (DSM-IV) as determined by the Structured Clinical Interview for the DSM-IV (SCID-IV), and non-dependent subjects scoring higher than 8 on AUDIT. Exclusion criteria are as indicated in the preceding examples.

All subjects are tested for baseline SCID-IV, AUDIT, PDQ, 90-day TLFB, DASS-21, PANAS, AUQ, FTND, body mass index (BMI), urine toxicology, bloods for baseline oxytocin and cortisol, liver function testing, heart rate (HR), blood pressure (BP), and ECG, and females are pregnancy-tested and their menstrual cycles determined, as described herein above for Study 2. Neuropsychological evaluations e.g., according to CANTAB are also performed. Additionally, subjects are subjected to attention bias assessment task testing, wherein attention biases to alcohol-related cues are determined using e.g., stroop and dot-probe methodology. Subjects also participate in a reward learning computer task, to assess motivation for their alcohol consumption. Based on their test results, subjects are selected for recruitment in the study.

Recruited subjects are administered placebo or oxytocin intranasally (80 IU per day: 40 IU at 9:00 am and 40 IU at 9:00 pm) over a period of 28 days, following completion of baseline measurements. Subjects are instructed on self-administration procedures and given an initial 14 day supply of medication. Participants attend a mid-point assessment where they will receive the remaining 14 day supply of medication. Drug administration commences on the evening of the day of the clinical and medical interview and ceases on a morning 28 days later, after 56 doses have been administered. Subjects are randomized to oxytocin-receiving or placebo-receiving groups, and the groups are stratified according to gender, age, and drinking behavior.

Recruited subjects are also fitted with an actigraphy watch and complete a sleep diary over the following two week period. The actigraphy watches provide information on sleep/wake cycles and light exposure which play an important role in the psychopathology of alcohol misuse. Participants also complete daily self-tests of drinking behavior (AUQ), mood (PANAS), and report on adverse effects of medication. All participants are contacted weekly beginning after 3 days from the commencement of therapy, to determine compliance and adverse events.

Subjects returning to the BMRI on the afternoon of the 14th day of testing are evaluated i.e., the mid-point assessment. Bloods are taken for analysis of plasma oxytocin and cortisol levels as well as basic pathology including liver function and compared to baseline levels before commencement of drug dosing. A urine toxicology test and alcohol breathalyzer test are also performed, to determine whether subjects have been alcohol-free and drug-free at the time of testing. Subjects are tested according to DASS-21, PANAS, 14-day TLFB, and AUQ, and neuropsychological evaluations e.g., according to CANTAB are performed. Changes in mood, drinking behavior and neuropsychology are evaluated for both groups by comparison with baseline evaluations. Changes in smoking behavior are evaluated by FTND testing and comparison with baseline evaluations. HR and BP, ECG, and BMI are recorded and compared to baseline levels before commencement of therapy.

On completion of the mid-point assessment, subjects are provided a further 14-day supply of oxytocin or placebo, and the procedure supra is repeated.

Subjects attend follow-up clinical and medical interviews at three-months, six-months and twelve-months following completion of the 28 day dosing regimen, and the same indices are determined.

Data are decoded and evaluated for the 28-day dosing regimen, and for the three-month, six-month and twelve-month follow-up periods. For example, both dependent and non-dependent drinkers exhibit decreased impulsivity and enhanced short-term memory function and general mood, as well as reduced alcohol intake e.g., to a level below that which is considered problematic or abusive. Alternatively, or in addition, subjects administered oxytocin in the double-blind study also report fewer heavy drinking days throughout the oxytocin dosing period and at 3-month follow-up and/or six-month follow-up and/or twelve-month follow-up than before therapy; and/or report a longer period of time between heavy drinking days throughout the oxytocin dosing period and at 3-month follow-up and/or six-month follow-up and/or twelve-month follow-up than before therapy and/or report more abstinent days throughout the oxytocin dosing period and at 3-month follow-up and/or six-month follow-up and/or twelve-month follow-up than before therapy and/or exhibit gradually improved liver function, BMI, and heart function during oxytocin dosing period and at 3-month follow-up and/or six-month follow-up and/or twelve-month follow-up, and/or do not meet the criteria for problem drinking e.g., alcohol dependence or heavy drinking at 3-month follow-up or 6-month follow-up or 12-month follow-up, and/or show improved sleep behavior throughout the medication dosing period and/or exhibit reduced cognitive biases to alcohol-related cues during oxytocin dosing period and at 3-month follow-up and/or six-month follow-up and/or twelve-month follow-up, and exhibit reduced reward driven motivation to consume alcohol during oxytocin dosing period and at 3-month follow-up and/or six-month follow-up and/or twelve-month follow-up. In contrast, subjects receiving the placebo show little or no statistical improvement during the dosing period or at 3-month follow-up and/or six-month follow-up and/or twelve-month follow-up, and show greater periods of relapse than subjects receiving oxytocin therapy.

We claim:

1. A method of reducing self-administration of alcohol in a subject suffering from problem drinking, said method comprising administering to the subject an amount of a composition comprising an oxytocin or an analog or derivative of the oxytocin set forth in SEQ ID NO: 1 or an oxytocin receptor agonist for a time and under conditions sufficient to reduce alcohol consumption by the subject at least to a level that constitutes moderate drinking behavior, thereby reducing self-administration of alcohol in the subject, wherein:

(a) said derivative of oxytocin is selected from the group consisting of: a fusion protein comprising SEQ ID NO: 1; and a peptide comprising SEQ ID NO: 1 and one or more-chemical moieties other than an amino acid;

(b) said analog of oxytocin is selected from the group consisting of: 4-serine,8-isoleucine-oxytocin; 3-phenylalanine-oxytocin (syn. oxypressin); 4-threonine-1-hydroxy-deaminooxytocin; 4-serine,8-isoleucine-oxytocin; 9-deamidooxytocin; 7-D-proline-oxytocin; (2,4-diisoleucine)-oxytocin; carbetocin (syn. 1-deamino-1-monocarba-[2-O-methyltyrosine]-oxytocin); 7-glycine-oxytocin; 4-threonine,7-glycine-oxytocin (syn. TG-OT); deamino-6-carba-oxytoxin (syn. dC60);

and deamino-dicarba-oxytocin (syn. 1-deamino-1,6-dicarba-[2-O-methyltyrosine]-oxytocin); and
(c) said oxytocin receptor agonist is selected from the group consisting of: 2-D-tyrosine-oxytocin; 5-D-asparagine-oxytocin; and 1-hemi-D-cysteine-oxytocin,
and wherein said moderate drinking behavior comprises a maximum alcohol intake that is less than that constituted by said problem drinking, wherein:
(i) said problem drinking is a drinking behavior comprising less than two alcohol-free days in any one-week period, and said moderate drinking behavior comprises at least two alcohol-free days in any one-week period; or
(ii) said problem drinking is a drinking behavior comprising alcohol intake sufficient to reach a blood alcohol level of 0.05% or higher on two or more consecutive days in any one-week period, and said moderate drinking behavior comprises a maximum alcohol intake that is insufficient to reach a blood alcohol level of 0.05% on two or more consecutive days in any one-week period; or
(iii) said problem drinking is a heavy drinking behavior comprising alcohol intake equivalent of at least 250 grams of alcohol for a male or at least 90 grams of alcohol for a female on one day in a one-week period, and said moderate drinking behavior comprises a maximum alcohol intake that is less than that constituted by said heavy drinking.

2. The method according to claim 1, wherein the subject is a chronic or heavy drinker as determined by a score of higher than 8 in the Alcohol Use Disorders Identification Test (AUDIT).

3. The method according to claim 1, wherein the subject has no apparent alcohol dependency.

4. The method according to claim 3, wherein the subject is a non-dependent problem drinker.

5. The method according to claim 1, wherein the subject suffers from an alcohol dependence syndrome.

6. The method according to claim 1, wherein the subject exhibits a problem drinking behavior and wherein the administration of oxytocin or an analog or derivative thereof or an oxytocin receptor agonist reduces alcohol intake by the subject to the level constituting moderate drinking behaviour.

7. The method according to claim 1, wherein the administration of oxytocin or an analog or derivative thereof or an oxytocin receptor agonist reduces alcohol intake by the subject by at least about 10%.

8. The method according to claim 1, wherein the administration of oxytocin or an analog or derivative thereof or an oxytocin receptor agonist reduces alcohol intake by the subject by at least about 30%.

9. The method according to claim 1, wherein the subject has a family history of problem drinking, alcoholism or alcohol misuse that renders the subject susceptible to developing problem drinking behavior.

10. A method of enhancing abstinence from alcohol in a subject in relapse from problem drinking by reducing self-administration of alcohol by the subject, said method comprising administering an amount of a composition comprising an oxytocin or an analog or derivative of the oxytocin set forth in SEQ ID NO: 1 or an oxytocin receptor agonist for a time and under conditions sufficient to enhance abstinence from alcohol by the subject, wherein:
(a) said derivative of oxytocin is selected from the group consisting of: a fusion protein comprising SEQ ID NO: 1; and a peptide comprising SEQ ID NO: 1 and one or more-chemical moieties other than an amino acid;
(b) said analog of oxytocin is selected from the group consisting of: 4-serine,8-isoleucine-oxytocin; 3-phenylalanine-oxytocin (syn. oxypressin); 4-threonine-1-hydroxy-deaminooxytocin; 4-serine,8-isoleucine-oxytocin; 9-deamidooxytocin; 7-D-proline-oxytocin; (2,4-diisoleucine)-oxytocin; carbetocin (syn. 1-deamino-1-monocarba-[2-O-methyltyrosine]-oxytocin); 7-glycine-oxytocin; 4-threonine,7-glycine-oxytocin (syn. TG-OT); deamino-6-carba-oxytoxin (syn. dC60); and deamino-dicarba-oxytocin (syn. 1-deamino-1,6-dicarba-[2-O-methytyrosine]-oxytocin); and
(c) said oxytocin receptor agonist is selected from the group consisting of: 2-D-tyrosine-oxytocin; 5-D-asparagine-oxytocin; and 1-hemi-D-cysteine-oxytocin, and wherein said problem drinking is:
(i) a drinking behavior comprising less than two alcohol-free days in any one-week period; or
(ii) a drinking behavior comprising alcohol intake sufficient to reach a blood alcohol level of 0.05% or higher on two or more consecutive days in any one-week period; or
(iii) a heavy drinking behavior comprising alcohol intake equivalent of at least 250 grams of alcohol for a male or at least 90 grams of alcohol for a female on one day in a one-week period.

11. The method according to claim 1, wherein the oxytocin is a peptide comprising an amino acid sequence set forth in SEQ ID NO: 1.

12. The method according to claim 1, wherein the oxytocin is 9-amido-oxytocin.

13. The method according to claim 1, wherein the oxytocin is 1-hydroxy-deaminooxytocin.

14. The method of claim 10, wherein the administration of oxytocin or an analog or derivative thereof or an oxytocin receptor agonist to the subject enhances abstinence from alcohol by the subject without adverse withdrawal symptom(s).

15. The method according to claim 1, wherein said method comprises administering to the subject an amount of the composition comprising the oxytocin or the analog or the derivative or the oxytocin receptor agonist for a time and under conditions sufficient to reduce alcohol consumption by the subject to a level that constitutes moderate drinking behaviour.

16. The method of according to claim 1, wherein the moderate drinking behavior comprises a maximum alcohol intake that is less than that constituted by said problem drinking set forth in (i), (ii) and (iii).

\* \* \* \* \*